US012648724B2

(12) United States Patent
Tsujikawa et al.

(10) Patent No.: US 12,648,724 B2
(45) Date of Patent: Jun. 9, 2026

(54) INFORMATION PROCESSING DEVICE, CONTROL METHOD, AND STORAGE MEDIUM

(71) Applicant: NEC Corporation, Tokyo (JP)

(72) Inventors: Masanori Tsujikawa, Tokyo (JP); Terumi Umematsu, Tokyo (JP); Kei Shibuya, Tokyo (JP)

(73) Assignee: NEC CORPORATION, Tokyo (JP)

( * ) Notice: Subject to any disclaimer, the term of this patent is extended or adjusted under 35 U.S.C. 154(b) by 608 days.

(21) Appl. No.: 18/020,568

(22) PCT Filed: Aug. 14, 2020

(86) PCT No.: PCT/JP2020/030882

§ 371 (c)(1),
(2) Date: Feb. 9, 2023

(87) PCT Pub. No.: WO2022/034682

PCT Pub. Date: Feb. 17, 2022

(65) Prior Publication Data

US 2023/0301572 A1 Sep. 28, 2023

(51) Int. Cl.
*A61B 5/16* (2006.01)

(52) U.S. Cl.
CPC ..................................... *A61B 5/165* (2013.01)

(58) Field of Classification Search
CPC ....... A61B 5/0077; A61B 5/112; A61B 5/165; A61B 5/167; A61B 5/486; A61B 5/746;
(Continued)

(56) References Cited

U.S. PATENT DOCUMENTS 5,724,987 A * 3/1998 Gevins ................. A61B 5/7264
434/258
6,416,472 B1 * 7/2002 Cady ........................ A61B 5/16
128/920
(Continued)

FOREIGN PATENT DOCUMENTS

JP 2002-529120 A 9/2002
WO 2018/069852 A1 5/2018
(Continued)

OTHER PUBLICATIONS

JP Office Action for JP Application No. 2022-542561, mailed on Mar. 19, 2024 with English Translation.
(Continued)

*Primary Examiner* — Milap Shah
(74) *Attorney, Agent, or Firm* — Sughrue Mion, PLLC

(57) ABSTRACT

An information processing device may include a first acquisition means, a second acquisition means, and an estimation means. The first acquisition means acquires a measurement result of an intellectual ability of a measurement target person. The second acquisition means acquires an estimation result of a mental state of the measurement target person, the mental state affecting the measurement of the intellectual ability. The estimation means estimates the intellectual ability based on the measured result of intellectual ability and the estimation result of the mental state. The information processing device can support decision-making based on the estimation result of the intellectual ability.

11 Claims, 16 Drawing Sheets

(58) Field of Classification Search

CPC ... A61B 5/4064; A61B 5/4088; A61B 5/7267; A61B 5/7278; A61B 5/7803; G10L 17/26; G16H 20/30; G16H 10/60; G16H 50/30; G06V 40/174

See application file for complete search history.

(56)  References Cited

U.S. PATENT DOCUMENTS

| | | | | |
|---|---|---|---|---|
| 6,434,419 | B1 * | 8/2002 | Gevins | G16H 50/20 |
| | | | | 600/544 |
| 11,278,230 | B2 * | 3/2022 | Connolly | A61B 5/4064 |
| 2001/0021800 | A1 * | 9/2001 | Balkin | A61B 5/16 |
| | | | | 128/920 |
| 2002/0017994 | A1 * | 2/2002 | Balkin | A61B 5/4806 |
| | | | | 340/573.1 |
| 2002/0192624 | A1 * | 12/2002 | Darby | A61B 5/165 |
| | | | | 434/236 |
| 2004/0210159 | A1 * | 10/2004 | Kibar | A61B 5/165 |
| | | | | 128/898 |
| 2004/0267570 | A1 * | 12/2004 | Becker | A61B 5/165 |
| | | | | 705/2 |
| 2006/0212090 | A1 * | 9/2006 | Lozano | A61N 1/36071 |
| | | | | 607/45 |
| 2009/0155754 | A1 * | 6/2009 | Shankle | G09B 7/00 |
| | | | | 434/236 |
| 2010/0086215 | A1 * | 4/2010 | Bartlett | G06V 40/20 |
| | | | | 382/224 |
| 2013/0080215 | A1 * | 3/2013 | Kawai | G06Q 10/06395 |
| | | | | 705/7.41 |
| 2014/0019059 | A1 * | 1/2014 | Shankle | G16H 50/20 |
| | | | | 702/19 |
| 2017/0311864 | A1 * | 11/2017 | Manabe | A61B 5/0077 |
| 2018/0070823 | A1 * | 3/2018 | Blackwell | A61B 5/1118 |
| 2018/0125404 | A1 * | 5/2018 | Bott | H04N 23/64 |
| 2018/0232567 | A1 * | 8/2018 | Dolsma | G09B 7/04 |
| 2018/0303397 | A1 * | 10/2018 | Krupat | A61B 5/165 |
| 2019/0130077 | A1 * | 5/2019 | De | G16H 50/30 |
| 2019/0231247 | A1 * | 8/2019 | Bernier | A61B 5/742 |
| 2021/0313070 | A1 | 10/2021 | Toyoshiba et al. | |
| 2021/0366613 | A1 * | 11/2021 | Schler | G06V 10/764 |
| 2024/0138750 | A1 * | 5/2024 | Umematsu | A61B 5/7282 |

FOREIGN PATENT DOCUMENTS

| | | | |
|---|---|---|---|
| WO | 2018/179292 | A1 | 10/2018 |
| WO | 2020/054186 | A1 | 3/2020 |

OTHER PUBLICATIONS

International Search Report for PCT Application No. PCT/JP2020/030882, mailed on Nov. 2, 2020.

* cited by examiner

100:COGNITIVE FUNCTION EXAMINATION SYSTEM

FIG. 11

EXAM RESULT VIEW    NIHON TARO   AGE 78

63

CURRENT CONDITION IS NOT SUITABLE FOR COGNITIVE EXAM.
PLEASE TRY AGAIN AFTER A WHILE.

64

| COGNITIVE FUNCTION SCORE : MEASURED VALUE | DEGREE OF AROUSAL | COGNITIVE FUNCTION SCORE : ESTIMATE VALUE | NORMAL VALUE |
|---|---|---|---|
| 18／30 | 2／10 | — | 26～ |

INFORMATION PROCESSING DEVICE, CONTROL METHOD, AND STORAGE MEDIUM

This application is a National Stage Entry of PCT/JP2020/030882 filed on Aug. 14, 2020, the contents of all of which are incorporated herein by reference, in their entirety.

TECHNICAL FIELD

The present disclosure relates to a technical field of an information processing device, a control method, and a storage medium configured to perform processing relating to estimation of a mental state.

BACKGROUND ART

Mini Mental State Examination (MMSE) and the like are known as a cognitive function examination for determining mild cognitive impairment and major neurocognitive disorder. Patent Literature 1 discloses a system configured to display a predetermined image and calculate the score of the cognitive function based on the movement of the eyeball when the target person watches the image. In addition, Patent Literature 2 discloses a system for predicting the severity of major neurocognitive disorder by analyzing free conversation.

CITATION LIST

Patent Literature

Patent Literature 1: WO2018/089852
Patent Literature 2: WO2020/054186

SUMMARY

Problem to be Solved

The cognitive function is known to decrease by aging, but it could also temporarily decrease depending on the state of a target person (subject). However, Patent Literature 1 and Patent Literature 2 are silent on considering the state of the target person.

In view of the above-described issues, it is an object of the present disclosure to provide an information processing device, a control method, and a storage medium capable of suitably executing the estimation of the intellectual ability of a target person or the output of information relating to the intellectual ability.

Means for Solving the Problem

In one mode of the information processing device, there is provided an information processing device including:

a first acquisition means configured to acquire a measurement result of an intellectual ability of a measurement target person;

a second acquisition means configured to acquire an estimation result of a mental state of the measurement target person, the mental state affecting the measurement of the intellectual ability; and an estimation means configured to estimate the intellectual ability based on the measured result of intellectual ability and the estimation result of the mental state.

In one mode of the control method, there is provided a control method executed by a computer, the control method including:

acquiring a measurement result of an intellectual ability of a measurement target person;

acquiring an estimation result of a mental state of the measurement target person, the mental state affecting the measurement of the intellectual ability; and estimating the intellectual ability based on the measured result of intellectual ability and the estimation result of the mental state. It is noted that the term "computer" herein includes any electronic device (which includes a processor incorporated in the electronic device) and may be configured by a plurality of electronic devices.

In one mode of the storage medium, there is provided a storage medium storing a program executed by a computer, the program causing the computer to:

acquire a measurement result of an intellectual ability of a measurement target person;

acquire an estimation result of a mental state of the measurement target person, the mental state affecting the measurement of the intellectual ability; and estimate the intellectual ability based on the measured result of intellectual ability and the estimation result of the mental state.

Effect

An example advantage according to the present invention is to suitably execute the estimation of the intellectual ability of a target person or the output of information relating to the intellectual ability.

BRIEF DESCRIPTION OF THE DRAWINGS

FIG. 11 illustrates an example of the examination result screen image in the second example embodiment.

EXAMPLE EMBODIMENTS

Hereinafter, example embodiments relating to an information processing device, a control method, and a storage medium will be described with reference to the drawings.

First Example Embodiment

(1-1) System Configuration

Figure 1:
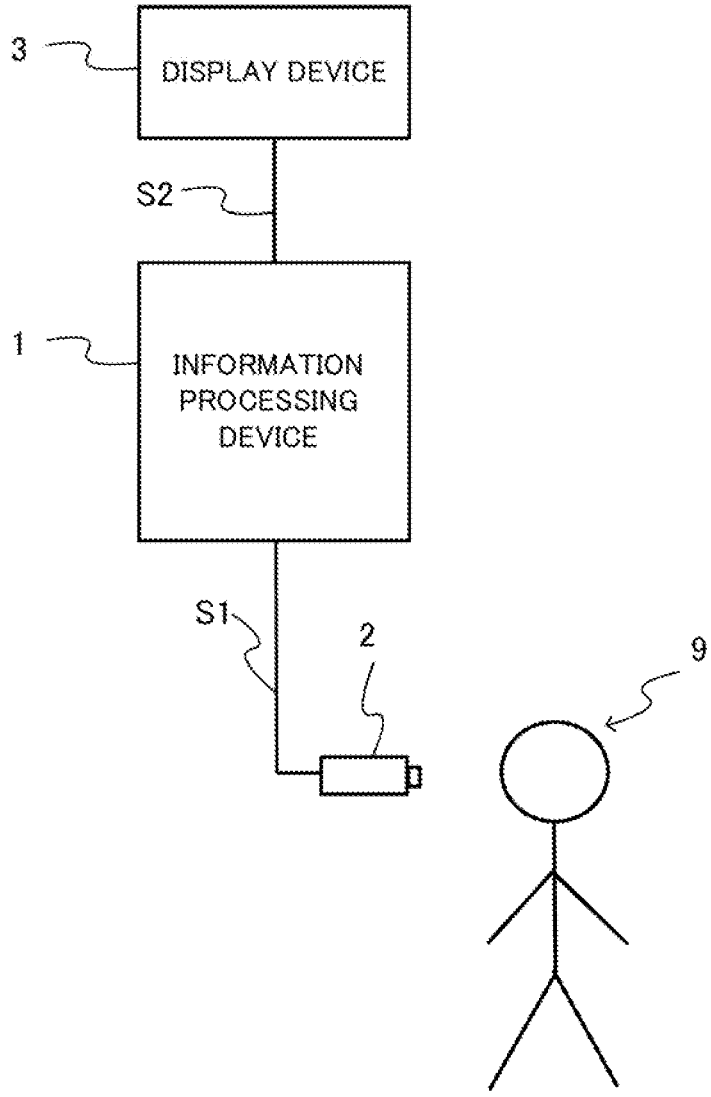
FIG. 1 illustrates a schematic configuration of a cognitive function examination system according to the first example embodiment.

FIG. 1 shows a schematic configuration of a cognitive function examination system 100 according to the first example embodiment. The cognitive function examination system 100 performs an examination (also referred to as "cognitive function examination") relating to cognitive function(s) of a measurement target person 9 and presents the examination result to the user. The cognitive function examination system 100 mainly includes an information processing device 1, a camera (imaging means) 2, and a display device 3.

The information processing device 1 performs data communication with the camera 2 and the display device 3 by communication through a communication network or by wireless or wired direct communication. Then, the information processing device 1 performs a simple cognitive function examination for the measurement target person 9 based on one or more captured images "S1" supplied from the cameras 2. Further, the information processing device 1 generates a display signal "S2" based on the examination result relating to the cognitive function of the measurement target person 9 and supplies the generated display signal S2 to the display device 3. The information processing device 1 may be a personal computer or may be a portable terminal such as a smartphone integrally configured with the camera 2 and the display device 3.

The camera 2 generates a captured image S1 and supplies the generated captured image S1 to the information processing device 1. The camera 2 may be a camera incorporated in the information processing device 1. The display device 3 displays information based on the display signal S2 supplied from the information processing device 1. Examples of the display device 3 include a display and a projector.

The configuration of the cognitive function examination system 100 shown in FIG. 1 is an example, and various changes may be made to the configuration. For example, the cognitive function examination system 100 may further include an input device (including a voice input device) configured to accept a user input by the measurement target person 9 or the like, or an audio output device configured to output a guidance, a warning sound, or the like. Further, the information processing device 1 may be configured by a plurality of devices. In this case, the plurality of devices constituting the information processing device 1 performs transmission and reception of information necessary for executing preassigned processing among the plurality of devices. In this case, the information processing device 1 functions as an information processing system.

(1-2) Hardware Configuration of Information Processing Device

Figure 2:
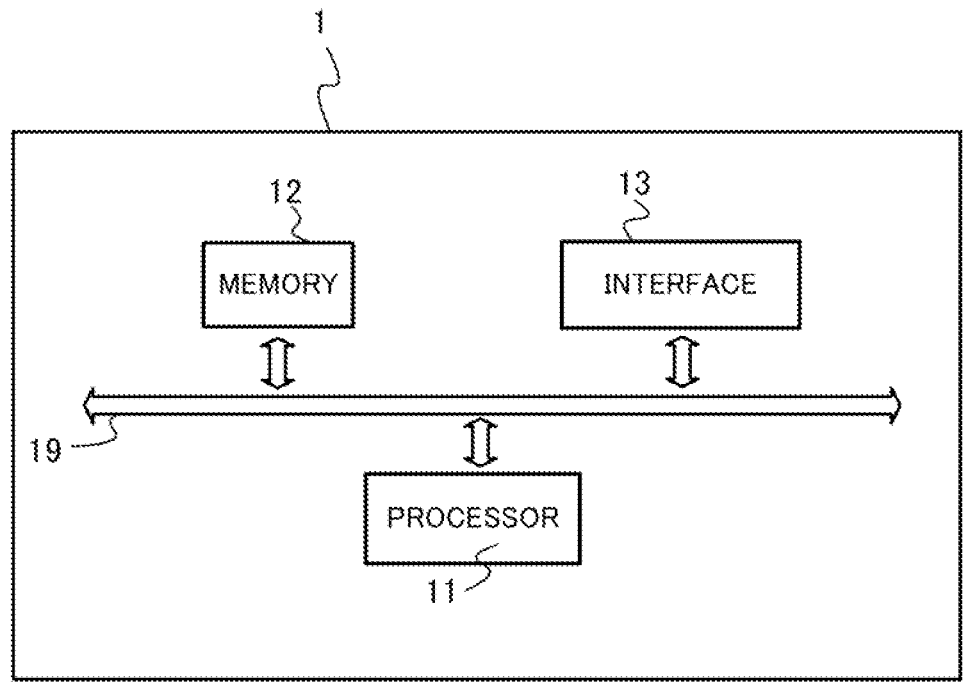
FIG. 2 illustrates the hardware configuration of an information processing device.

FIG. 2 illustrates a hardware configuration of the information processing device 1. The information processing device 1 includes a processor 11, a memory 12, and an interface 13 as hardware. The processor 11, the memory 12 and the interface 13 are connected to one another via a data bus 19.

The processor 11 functions as a controller (arithmetic unit) configured to control the entire information processing unit 1 by executing a program stored in the memory 12. The processor 11 is one or more processors and examples thereof include a CPU (Central Processing Unit), a GPU (Graphics Processing Unit), a TPU (Tensor Processing Unit), and a quantum processor. The processor 11 may be configured by a plurality of processors. The processor 11 is an example of a computer.

The memory 12 is configured by a variety of volatile and non-volatile memories, such as a RAM (Random Access Memory), a ROM (Read Only Memory), and a flash memory. Further, a program for executing a process to be executed by the information processing device 1 is stored in the memory 12. Further, for example, the memory 12 includes parameter information for use in estimating the cognitive function and estimating a particular mental state, respectively. A part of the information stored in the memory 12 may be stored by one or more external storage devices configured to communicate with the information processing device 1, or may be stored by a storage medium removable from the information processing device 1. The above-described external storage device may be one or more server devices configured to perform data communication with the information processing device 1.

The interface 13 is one or more interfaces for electrically connecting the information processing device 1 to other devices. These interfaces may include a wireless interface, such as a network adapter, for transmitting and receiving data to and from other devices wirelessly, and a hardware interface, such as cables, for connecting the device to other devices.

The hardware configuration of the information processing device 1 is not limited to the configuration shown in FIG. 2. For example, the information processing device 1 may incorporate at least one of the camera 2 or the display device 3.

(1-3) Functional Block

Next, a specific processing to be performed by the information processing device 1 will be described. In summary, the information processing device 1 measures the cognitive function of the measurement target person 9 while estimating the mental state that affects the measurement of the cognitive function, and then estimates the cognitive function of the measurement target person 9 based on the measurement result and the estimation result. Then, the information processing device 1 displays information on the estimation result of the cognitive function of the measurement target person 9 on the display device 3.

Figure 3:
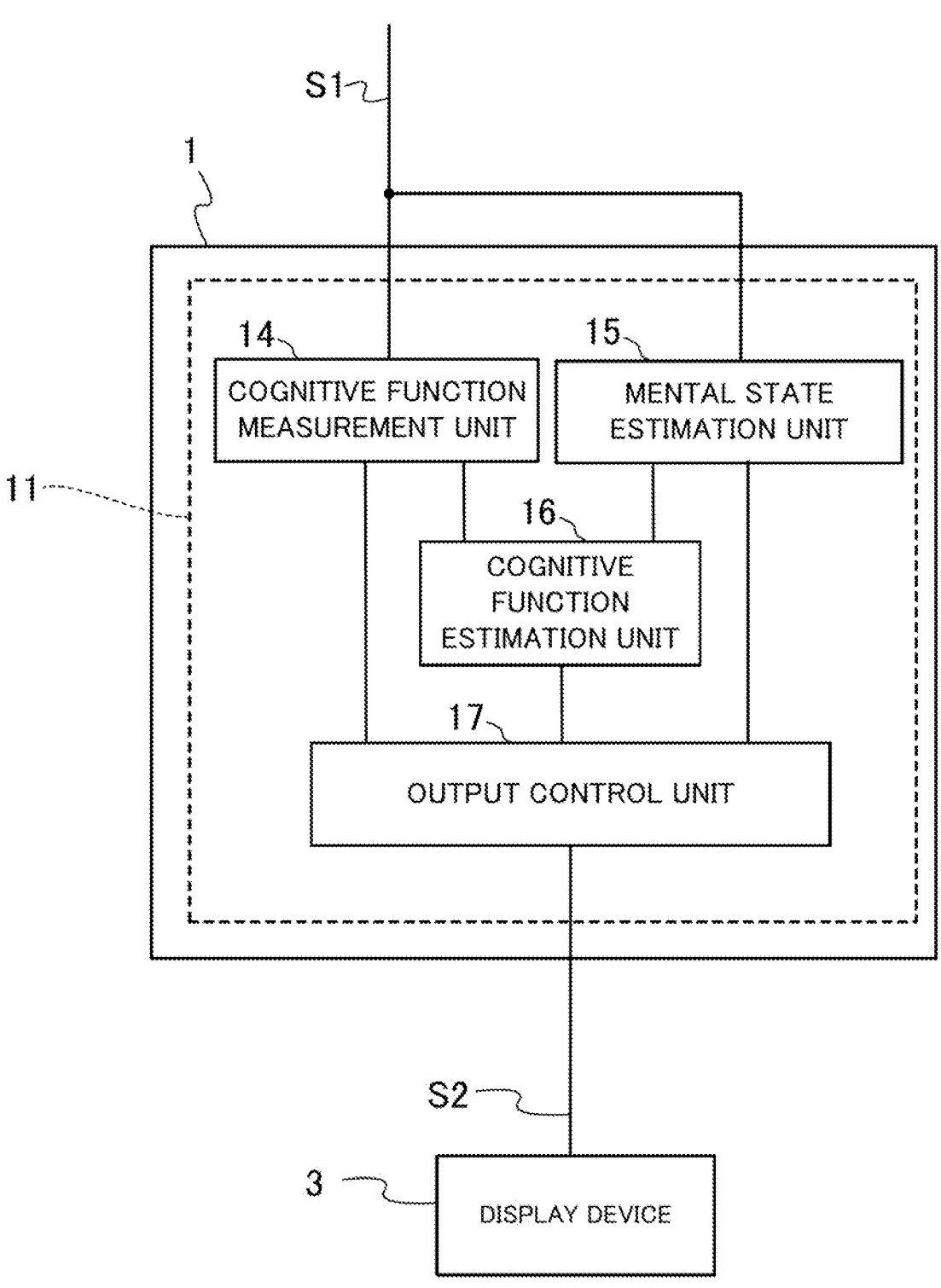
FIG. 3 illustrates an example of a functional block of the information processing device.

FIG. 3 illustrates an example of a functional block of the information processing device 1. The processor 11 of the information processing device 1 functionally includes a cognitive function measurement unit 14, an mental state estimation unit 15, a cognitive function estimation unit 16, and an output control unit 17. In FIG. 3, any two blocks to transmit and receive data are connected by a solid line, but the combinations of the blocks to transmit and receive data is not limited to the combinations shown in FIG. 3. The same applies to the drawings of other functional blocks described below.

The cognitive function measurement unit 14 measures the cognitive function on the basis of the captured image S1 supplied from the camera 2 through the interface 13 and supplies the measured result to the cognitive function estimation unit 16 and the output control unit 17, respectively. In this case, based on the captured image S1, the cognitive function measurement unit 14 calculates a score (also referred to as "cognitive function measurement score Sm") regarding the cognitive function of the measurement target person 9 as the above-described measurement result. The cognitive function measurement score Sm is, for example, a comprehensive score (total score) regarding cognitive functions of the measurement target person 9. The cognitive function measurement score Sm may further include a score (also referred to as "function-specific score") of a function-specific cognitive capability for each function, in addition to the above-described total score. The function-specific scores are, for example, scores for language understanding, perceptual integration, working memory, and processing speed, respectively.

A supplemental description will be given of the method of calculating the cognitive function measurement score Sm based on the captured image S1. For example, first, the cognitive function measurement unit 14 causes the display device 3 to display a screen image for a predetermined examination on the display device 3 by supplying the captured image S1 via the interface 13 to the display device 3. Then, the cognitive function measurement unit 14 analyzes the movement of the eyeball(s) (including the sclera, the iris, and the pupil) of the measurement target person 9 based on the captured image S1 obtained by capturing an image of the measurement target person 9 who is visually recognizing the screen image. Thus, the cognitive function measurement unit 14 calculates the cognitive function measurement score Sm obtained by scoring the cognitive function of the measurement target person 9. A technique for scoring a cognitive function of a subject by analyzing an image of a movement of eyeball(s) of the subject is disclosed in, for example, Patent Literature 1.

The mental state estimation unit 15 estimates the mental state at the time of measurement of the cognitive function of the measurement target person 9 based on the captured image S1 supplied from the camera 2 and supplies the estimation result to the cognitive function estimation unit 16 and the output control unit 17, respectively. In this case, the mental state to be estimated is the mental state of the measurement target person 9 that affects the measurement of the cognitive function and fluctuates in the short-term cycles. In the present example embodiment, the mental state estimation unit 15 estimates the degree of arousal that is one of indices that represents the mental state that affects the measurement of the cognitive function and fluctuates in the short-term cycles. In this case, the mental state estimation unit 15 analyzes the captured image S1 to recognize the movement or the facial expression of the eyelid of the measurement target person 9 and estimates the scored degree of arousal of the measurement target person 9 at the time of measurement of the cognitive function based on the recognition result. The mental state estimation unit 15 may estimate the degree of stress of the measurement target person 9, the degree of sleepiness thereof, the pulse (heart rate) thereof, the degree of concentration thereof, the type of emotion thereof, or the degree of alcohol included in the measurement target person 9, instead of the degree of arousal thereof. In this case, as the "type of emotion" described above, for example, the mental state estimation unit 15 may estimate the class to which the emotion of the measurement target person 9 belongs among a plurality of pre-classified classes of the emotion.

The cognitive function measurement unit 14 and the mental state estimation unit 15 may calculate the cognitive function measurement score Sm and the degree of arousal by using inference engines that are learned in advance based on machine learning such as deep learning, respectively. In this case, for example, the inference engine to be used by the cognitive function measurement unit 14 is a machine learning model learned by use of input data and correct answer data, wherein the input data is a predetermined number of images obtained by imaging a measurement target person and the correct answer data is the score of the cognitive function of the measurement target person at the time of generating the images. The score of the cognitive function to be used as the correct answer data in this case may be identified based on an arbitrary method of the examination of the cognitive function. The inference engine to be used by the mental state estimation unit 15 is a machine learning model learned by use of input data and correct answer data, wherein the input data is a predetermined number of images obtained by photographing a measurement target person and the correct answer data is the degree of arousal of the measurement target person at the time of generating the images. The degree of arousal to be used as the correct answer data may be measured by one or more sensors or may be estimated based on a questionnaire or the like. The parameters of the inference engine obtained by the learning are stored in advance in the memory 12 or the like. When the machine learning model described above is a neural network such as a convolution neural network, various parameters relating to the layer structure, the neuron structure of each layer, the number of filters and the size of filters in each layer, and the weight of each element of each filter are stored in the memory 12.

The cognitive function estimation unit 16 estimates the cognitive function of the measurement target person 9 based on the measurement result of the cognitive function of the measurement target person 9 generated by the cognitive function measurement unit 14 and the estimation result of the degree of arousal of the measurement target person 9 generated by the mental state estimation unit 15. Specifically, based on the estimated degree of arousal, the cognitive function estimation unit 16 corrects the cognitive function measurement score Sm that is the measurement result of the cognitive function of the measurement target person 9. Hereafter, the score of the cognitive function obtained by correcting the cognitive function measurement score Sm is also referred to as "cognitive function estimation score Se". Specific methods for calculating the cognitive function estimation score Se are described in detail in the section "(1-4) "Calculation of Cognitive Function Estimation Score". The cognitive function estimation unit 16 supplies the cognitive function estimation score Se that is the estimation result of the cognitive function of the measurement target person 9 to the output control unit 17.

In such a case that the cognitive function measurement score Sm includes the total score of the cognitive functions and the function-specific score regarding each function, the cognitive function estimation unit 16 may correct each of them based on the estimated degree of arousal. In this case, the cognitive function estimation unit 16 calculates the cognitive function estimation score Se that indicates the estimate value of the total score of the cognitive functions and the estimated values of the respective function-specific scores.

The output control unit 17 controls the display device 3 to display the examination result relating to the cognitive function of the measurement target person 9 on the basis of the estimation result or the measurement result supplied from the cognitive function measurement unit 14, the mental state estimation unit 15, and the cognitive function estimation unit 16, respectively. In this instance, the output control unit 17 generates a display signal S2 based on the above-described estimation result and measurement result and supplies the generated display signal S2 to the display device 3 via the interface 13. Information to be displayed on the display device 3 will be described later in the section "(1-5) Examination Result Screen Image". The viewer of the information displayed on the display device 3, for example, may be the measurement target person 9, or may be a medical person who diagnoses illness of the measurement target person 9.

It is noted that each component corresponding to the cognitive function measurement unit 14, the mental state estimation unit 15, the cognitive function estimation unit 16 and the output control unit 17 described in FIG. 3 can be realized by the processor 11 executing a program, for example. Additionally, the necessary programs may be recorded on any non-volatile storage medium and installed as necessary to realize each component. It should be noted that at least a portion of each of these components may be implemented by any combination of hardware, firmware, and software, without being limited to being implemented by software based on a program. At least some of these components may also be implemented using user programmable integrated circuit such as, for example, a FPGA (Field-Programmable Gate Array) and a microcontroller. In this case, the integrated circuit may be used to realize a program functioning as each of the above components. Further, at least a part of the components may be configured by ASSP (Application Specific Standard Produce) or ASIC (Application Specific Integrated Circuit). Thus, each of the above-described components may be realized by various hardware. Furthermore, each of these components may be implemented by cooperation of a plurality of computers, for example, using cloud computing technology. The above is true for other example embodiments described later.

(1-4) Calculation of Cognitive Function Estimation Score

Next, a description will be given of the methods of calculating the cognitive function estimation score Se by the cognitive function estimation unit 16. Schematically, the cognitive function estimation unit 16 calculates the cognitive function estimation score Se that is the cognitive function measurement score Sm corrected based on the degree of exertion (performance) of the cognitive function of the measurement target person 9, wherein the degree of exertion is estimated based on the degree of arousal estimated by the mental state estimation unit 15. Thereby, the cognitive function estimation unit 16 outputs the estimation result of the cognitive function independent of the degree of arousal during the measurement of the measurement target person 9.

First, a description will be given with reference to FIG. 4 of a general relation between the cognitive function and the degree of arousal that is a premise in the estimation process to be executed by the cognitive function estimation unit 16.

Figure 4:
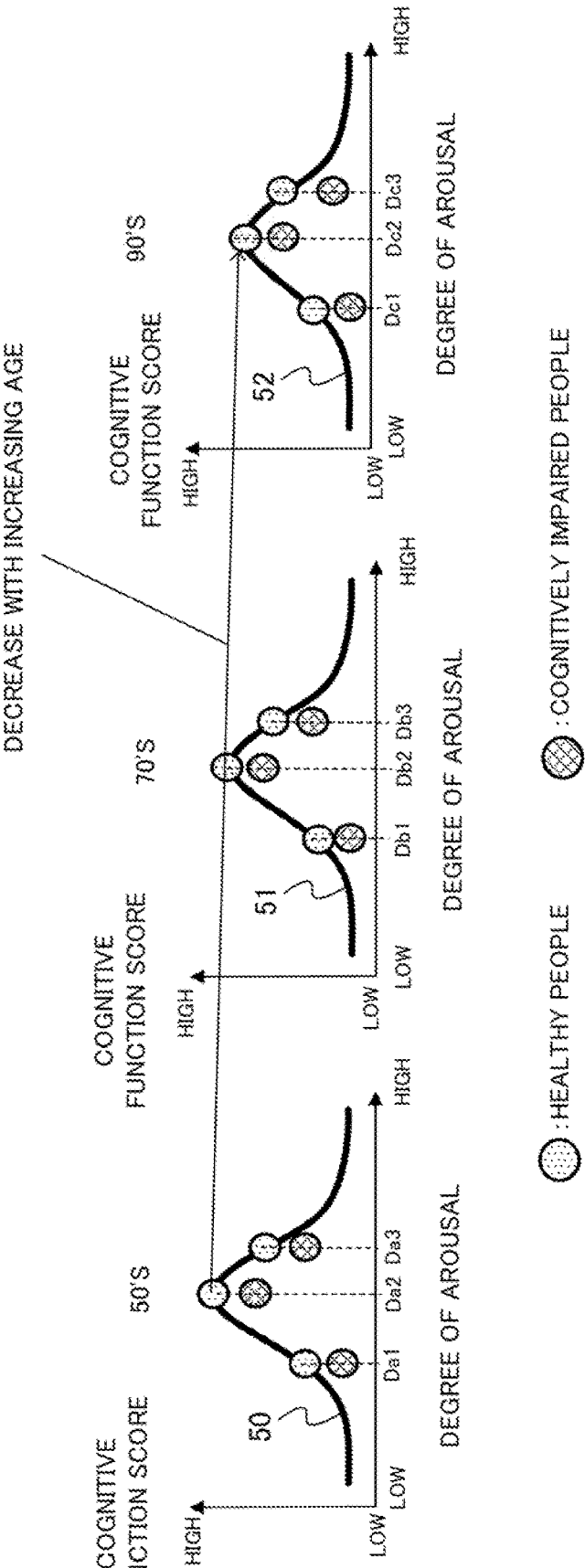
FIG. 4 illustrates a graph showing the relation between cognitive function and the degree of arousal depending on the age.

FIG. 4 is a diagram showing the age-specific relation between the cognitive function score and the degree of arousal. FIG. 4 shows the graphs 50 to S2 indicative of the relations between cognitive function score and the degree of arousal regarding general healthy people without any cognitive impairment on two-dimensional coordinates for people in their 50s, 70s, and 90s, respectively. On these two-dimensional coordinates, cognitive function scores of healthy people and cognitively impaired people are plotted respectively when the degrees of arousal are "Da1" to "Da3", "Db1" to "Db3", and "Dc1" to "Dc3". Here, examples of the cognitively impaired people include a person with mild cognitive impairment (MCI: Mild Cognitive Impairment) and a person with major neurocognitive disorder.

As shown in the graphs 50 to 52, the degree of exertion of the cognitive function differs depending on the degree of arousal in any age groups. For example, for the people in their 50s, the cognitive function of healthy people in the degree of arousal "Da1" or "Da3" is lower than that of healthy people in the degree of arousal "Da2". In other words, the degree of exertion of the cognitive function when the degree of arousal is "Da1" or "Da3" is lower than the degree of exertion of the cognitive function when the degree of arousal is "Da2". Consequently, the cognitive function score of a healthy person at the time of such a degree of arousal (e.g., "Da1") that corresponds to a low degree of exertion of the cognitive function could be lower than the cognitive function score of a cognitively impaired person at the time of such a degree of arousal (e.g., "Da2") that corresponds to a high degree of exertion of the cognitive function.

Thus, for the people in their 50's, the measured cognitive function score depends on the degree of arousal at the time of the measurement. Similarly, for the people in their 70s and 90s, the measured cognitive function score depends on the degree of arousal during the measurement. These tendencies are consistent with Yerkes-Dodson law, which indicates that performance is highest at the moderate degree of arousal.

Taking the above into consideration, the cognitive function estimation unit 16 corrects the cognitive function measurement score Sm based on the degree of arousal at the time of measurement of the cognitive function measurement score Sm of the measurement target person 9. Specifically, the cognitive function estimation unit 16 estimates the degree of exertion of the cognitive function when compared with the reference arousal degree based on the estimated degree of arousal at the time of measurement of the cognitive function measurement score Sm, and corrects the cognitive function measurement score Sm according to the degree of performance.

Figure 5:
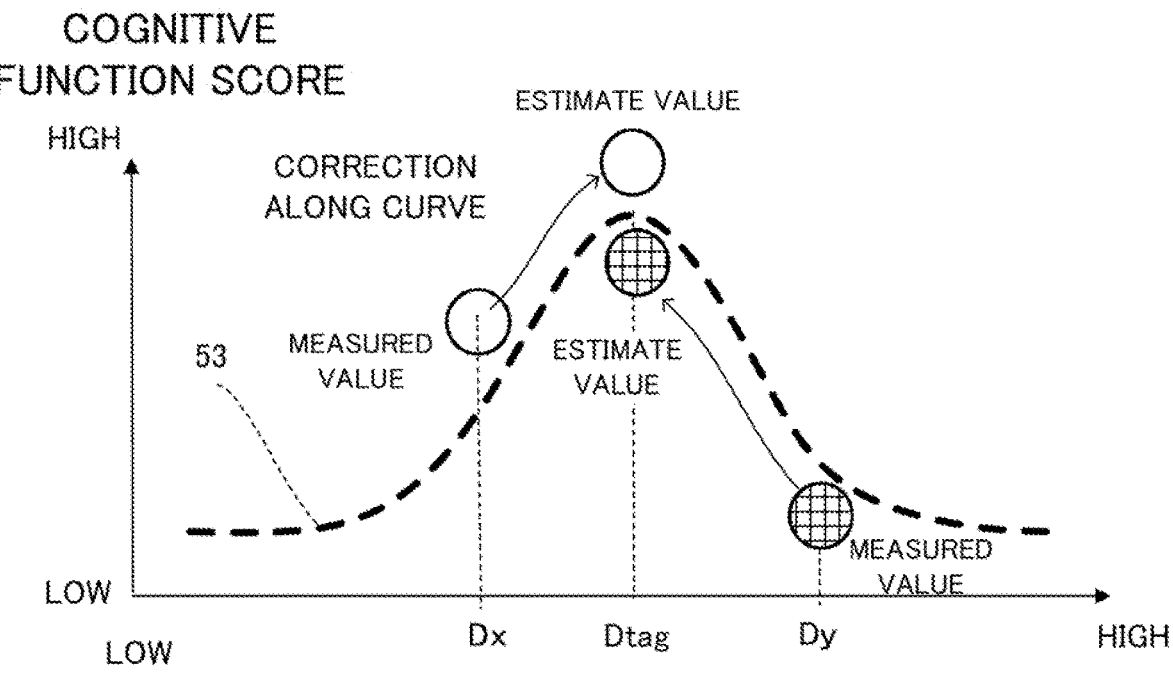
FIG. 5 is a diagram showing an outline of calculation of the cognitive function estimation score.

FIG. 5 is a diagram illustrating an outline of calculation of the cognitive function estimation score Se by the cognitive function estimation unit 16. FIG. 5 shows the graph 53 indicating the relation between the degree of arousal and the cognitive function score. The graph 53 is, for example, a statistical model obtained by applying a statistical technique such as regression analysis to samples of plural combinations of the cognitive function score and the degree of arousal measured for a plurality of subjects. In another example, the graph 53 may be a statistical model calculated by applying a statistical technique such as regression analysis to samples of plural combinations of the cognitive function score and the degree of arousal generated by multiple times measurements for a single subject.

Based on the relation shown in the graph 53, the cognitive function measurement score Sm, and the degree of arousal estimated at the time of the measurement of the cognitive function measurement score Sm, the cognitive function estimation unit 16 estimates the cognitive function estimation score Se that is the cognitive function score exerted in the state where the degree of arousal is the reference arousal degree "Dtag" which is a reference degree of arousal. Here, the reference arousal degree "Dtag" is, as an example, set to the degree of arousal when the cognitive function score is most exerted in the relation shown in the graph 53.

For example, when the degree of arousal at the time of the cognitive function examination of the measurement target person 9 is estimated to be "Dx" by the mental state estimation unit 15, the cognitive function estimation unit 16 corrects the cognitive function measurement score Sm on the basis of the difference or ratio between the cognitive function score at the degree-of-arousal Dx in the graph 53 and the cognitive function score at the reference arousal degree Dtag. In this instance, the cognitive function estimation unit 16 calculates the cognitive function estimation score Se that is a value obtained by adding the above-described difference to the cognitive function measurement score Sm or a value obtained by dividing the cognitive function measurement score Sm by the above-described ratio (in this case, less than 1). For example, when the ratio of the reference arousal degree Dtag to the degree-of-arousal Dx is "0.7", the cognitive function estimation unit 16 calculates the cognitive function estimation score Se that is a value obtained by dividing the cognitive function measurement score Sm by "0.7". Similarly, when the degree of arousal is estimated to be "Dy" by the mental state estimation unit 15, the cognitive function estimation unit 16 corrects the cognitive function measurement score Sm based on the difference or ratio between the cognitive function score at the degree-of-arousal Dy in the graph 53 and the cognitive function score at the reference arousal degree Dtag.

In this case, for example, a look-up table indicating the above-described difference or ratio for each possible degree of arousal that can be estimated by the mental state estimation unit 15 is stored in the memory 12 or the like. Then, the cognitive function estimation unit 16 calculates the cognitive function estimation score Se by specifying the above-described difference or ratio by referring to the look-up table. In another example, the cognitive function estimation unit 16 may calculate the cognitive function estimation score Se by specifying the above-described difference or ratio from the degree of arousal estimated by the mental state estimation unit 15 using an equation for obtaining the above-described difference or ratio from the degree of arousal. In yet another example, the cognitive function estimation unit 16 may derive the cognitive function estimation score Se from an equation or a look-up table to directly obtain, from input values indicative of the cognitive function measurement score Sm and the estimated degree of arousal, the cognitive function estimation score Se corrected in consideration of the above-described difference or ratio. It is also noted that the cognitive function estimation unit 16 may obtain the cognitive function estimation score Se by using an inference engine instead of using the above-mentioned look-up table or the equation, wherein the inference engine is learned based on machine learning such as deep learning to infer the cognitive function estimation score Se when the cognitive function measurement score Sm and the estimated degree of arousal are inputted to the inference engine.

The cognitive function estimation unit 16 may calculate the cognitive function estimation score Se in further consideration of the age of the measurement target person 9. As shown in FIG. 4, the relation between the degree of arousal and the cognitive function generally differs depending on the age of the measurement target person 9. Therefore, a statistical relation like the graph 53 between the cognitive function score and the degree of arousal is calculated for each predetermined age group, and the memory 12 may store the above-mentioned look-up table, the equation, or the inference engine for each age group based on the statistical relation. In this instance, the cognitive function estimation unit 16 or any other processing unit estimates the age of the measurement target person 9 by performing the age estimation including the process of analyzing the face or the like of the measurement target person 9 with respect to the captured image S1. When attribute information including the age of the measurement target person 9 registered before the cognitive function examination is previously stored in the memory 12 or the like, the cognitive function estimation unit 16 may specify the age of the measurement target person 9 by referring to the attribute information.

(1-5) Examination Result Screen Image

Figure 6:
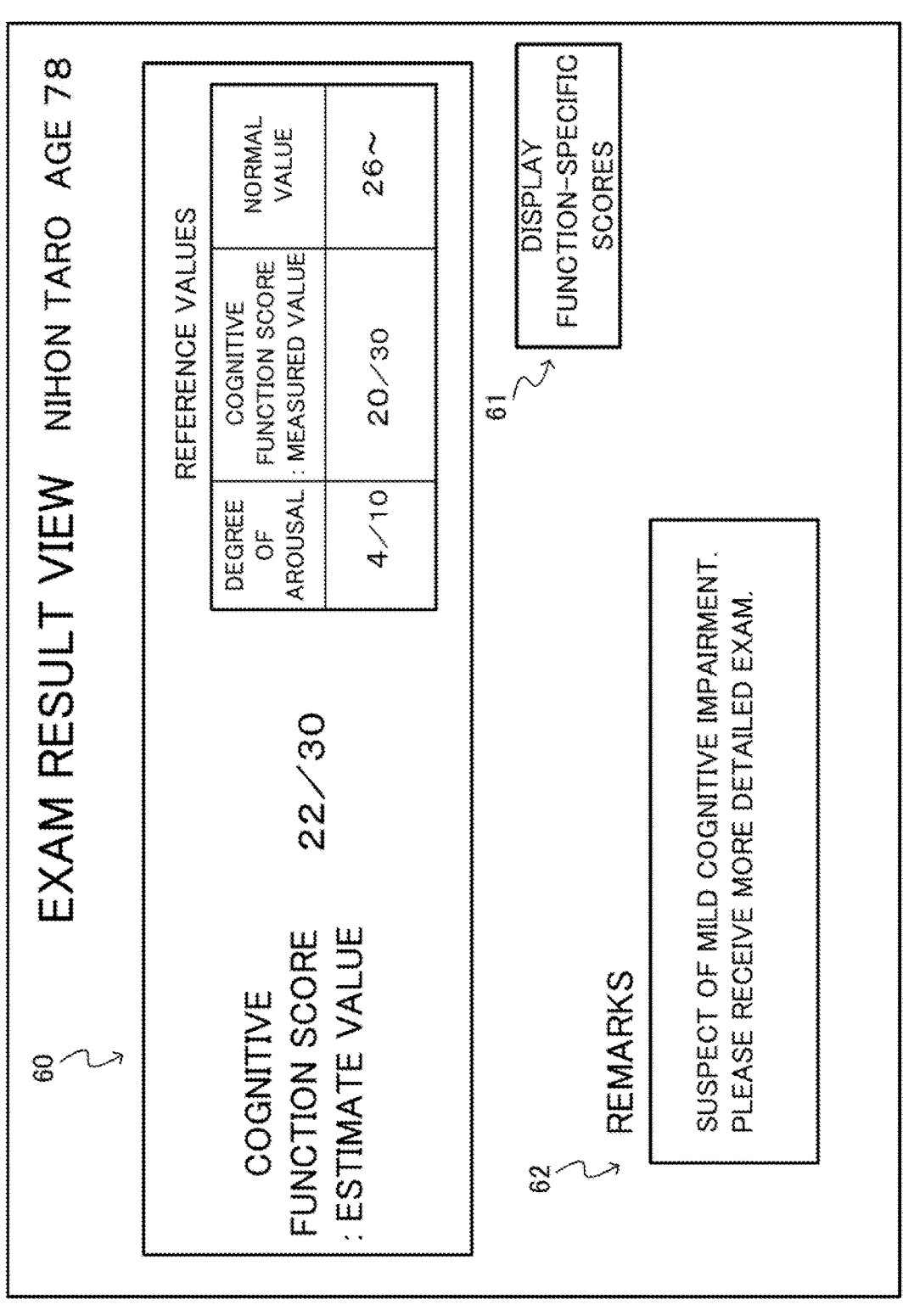
FIG. 6 illustrates an example of the examination result screen image according to the first example embodiment.

FIG. 6 illustrates an example of an examination result screen image which the output control unit 17 in the first example embodiment causes the display device 3 to display. Here, as an example, the measurement target person 9 is "Taro Japan" at 78 year old. The output control unit 17 generates a display signal S2 based on the information supplied from the cognitive function measurement unit 14, the mental state estimation unit 15, and the cognitive function estimation unit 16, and supplies the display signal S2 to the display device 3, thereby causing the display device 3 to display the examination result screen image shown in FIG. 6. The output control unit 17 mainly provides, on the examination result screen image, a score display field 60, a function-specific score request button 61, and a remarks display field 62.

The output control unit 17 displays, in the score display field 60, "cognitive function score (estimate value)" representing the estimated total cognitive function of the measurement target person 9 while displaying "cognitive function score (measured value)", "degree of arousal", and "normal value" as reference values. Here, the output control unit 17 displays the cognitive function estimation score Se (in this case, on a scale of 1 to 30) estimated by the cognitive function estimation unit 16 as "cognitive function score (estimate value)". The output control unit 17 displays a score (4 in this case) on a scale of 1 to 10 representing the degree of arousal estimated by the mental state estimation unit 15 as "degree of arousal". Further, the output control unit 17 displays, as "normal value", the value range (here, 26 or more on a scale of 1 to 30) of the cognitive function score to be regarded as a healthy person, wherein the value range is stored in advance in the memory 12 or the like. The value presented as the "normal value" may be a value that varies depending on the age group of the measurement target person 9.

The function-specific score request button 61 is a button for instructing the display of the function-specific score for each cognitive function of the measurement target person 9. When the output control unit 17 detects the selection of the function-specific score request button 61, it displays each function-specific score of the measurement target person 9. In this case, for example, the output control unit 17 displays the estimate value of the function-specific score on the examination result screen image for each cognitive function such as language understanding, perceptual integration, working memory, and processing speed.

The remarks display field 62 is a field for displaying comments on the cognitive function estimation score Se of the measurement target person 9. In the example shown in FIG. 6, since the cognitive function estimation score Se of the measurement target person 9 is out of the range of the normal value, the output control unit 17 displays a notice (warning) indicating that there is a suspect of mild cognitive impairment and that a more detailed examination should be received on the remarks display field 62. In this instance, the output control unit 17 determines text information to be displayed in the remarks display field 62 on the basis of the cognitive function estimation score Se. For example, a table that associates the cognitive function estimation score Se with the text information to be displayed in the remarks display field 62 is stored in the memory 12 or the like, and the output control unit 17 refers to the table and determines the text information to be displayed in the remarks display field 62 from the cognitive function estimation score Se.

By displaying the examination result screen image shown in FIG. 6, the output control unit 17 can suitably present a cognitive function estimation score Se independent of the mental state of the measurement target person 9 which varies in the short-term cycles to the viewer. The output control unit 17 can also suitably present comments and the like on various scores relating to cognitive functions and cognitive impairments in addition to the cognitive function estimation score Se to the viewer.

(1-6) Processing Flow

Figure 7:
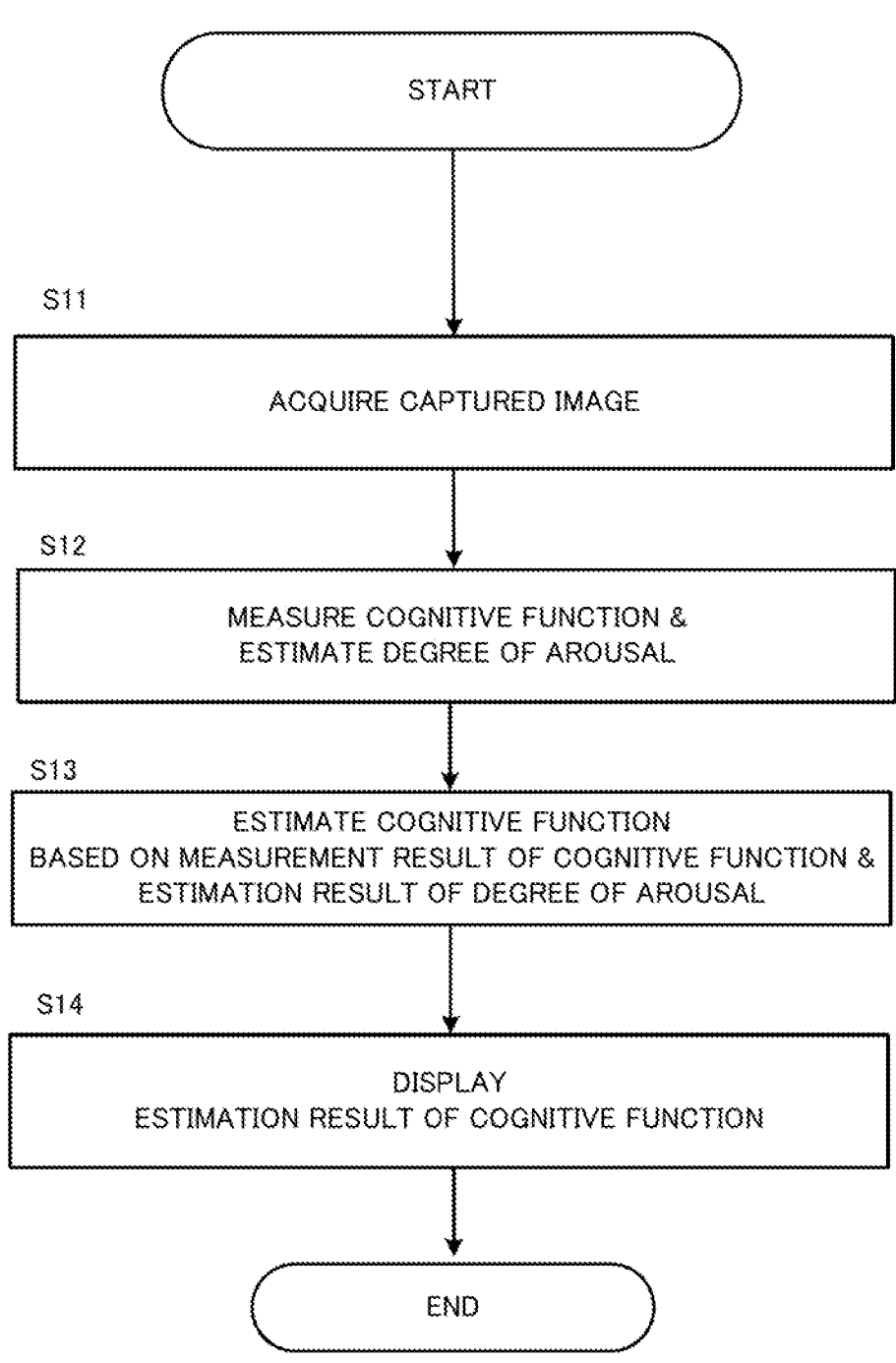
FIG. 7 illustrates an example of a flowchart showing a procedure of the process performed by the information processing device in the first example embodiment.

FIG. 7 is an example of a flowchart illustrating a procedure of the process to be executed by the information processing device 1 according to the first example embodiment. The information processing device 1 repeatedly executes the processing of the flowchart shown in FIG. 7.

First, the information processing device 1 acquires the captured image S1 generated by the camera 2 (step S11). In this case, for example, when the information processing device 1 detects that a person exists in the imaging range of the camera 2, it acquires the captured image S1 obtained by capturing the person as the measurement target person 9. In another example, the information processing device 1 may acquire the captured image S1 generated by the camera 2 at the timing specified by the user input. In this case, the user input may be an input based on an operation to the input device, or may be a voice input.

Then, the cognitive function measurement unit 14 of the information processing device 1 measures the cognitive function based on the captured image S1 acquired at step S11, and the mental state estimation unit 15 of the information processing device 1 estimates the degree of arousal based on the captured image S1 (step S12). Thereby, the cognitive function measurement unit 14 calculates the cognitive function measurement score Sm and the mental state estimation unit 15 calculates the estimated degree of arousal. The process executed by the cognitive function measurement unit 14 and the process executed by the mental state estimation unit 15 are in no particular order, and therefore either one may be executed first, or they may be executed simultaneously.

Then, the cognitive function estimation unit 16 estimates the cognitive function based on the measurement result of the cognitive function and the estimation result of the degree of arousal at step S12 (step S13). In this instance, the cognitive function estimation unit 16 calculates the cognitive function estimation score Se independent of the state (i.e., condition) of the measurement target person 9 based on the cognitive function measurement score Sm calculated by the cognitive function measurement unit 14 and the estimated degree of arousal calculated by the mental state estimation unit 15.

Then, the output control unit 17 displays the estimated result of the cognitive function on the display device 3 (step S14). In this instance, the output control unit 17 generates the display signal S2 based on the cognitive function estimation score Se or the like calculated at step S13 and supplies the display signal S2 to the display device 3 via the interface 13. Thereby, the output control unit 17 displays the examination result screen image or the like as shown in FIG. 6 on the display device 3.

(1-7) Technical Effect

Next, supplementary description will be given of technical effects in the first example embodiment.

As shown in FIG. 4, the decrease in cognitive functions occurs not only due to cognitive impairment but also due to aging, and also due to the change in the mental state of the measurement target person 9 in the short-term cycles. On the other hand, in a conventional method of cognitive function examination, since the mental state at the time of examination of the measurement target person 9 is not considered, there is an issue that it is impossible to distinguish whether the cognitive function is deteriorated due to the change in the mental state of the measurement target person 9 in the short-term cycles or the cognitive function is deteriorated due to the cognitive impairment of the measurement target person 9. In view of the above, in the first example embodiment, the information processing device 1 corrects the cognitive function measurement score Sm based on the degree of arousal at the time of examination of the measurement target person 9. Thus, the information processing device 1 can suitably calculate the cognitive function estimation score Se independent of the mental state of the measurement target person 9 changing in the short-term cycles.

(1-8) Modifications

Next, a description will be given of preferred modifications of the first example embodiment. The following modifications may be applied in combination.

First Modification

The information processing device 1 may perform measurement of the cognitive function of the measurement target person 9 and estimation of the mental state affecting the measurement based on information other than the image obtained by imaging the measurement target person 9.

Figure 8:
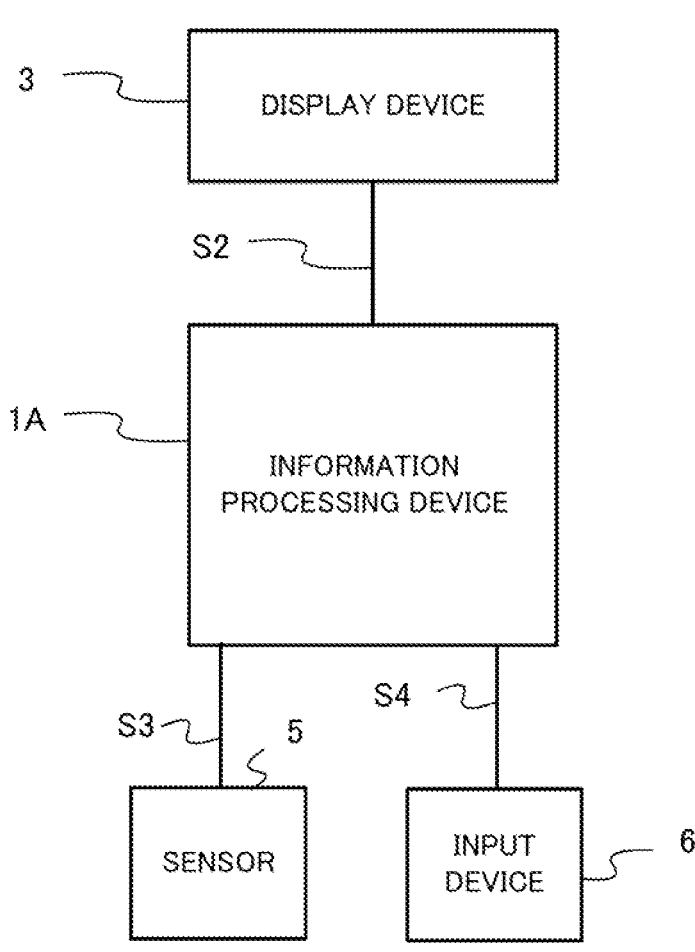
FIG. 8 illustrates a schematic configuration of a cognitive function examination system according to a first modification.

FIG. 8 shows a schematic configuration diagram of a cognitive function examination system 100A according to the first modification. The cognitive function examination system 100A shown in FIG. 8 includes a sensor 5 and an input device 6.

The sensor 5 is, for example, a wearable sensor worn by the measurement target person 9, and measures the biometric signal or the like of the measurement target person 9, and supplies the measured biometric signal or the like to the information processing device 1A as a sensor signal S3. In this instance, examples of the sensor signal S3 include heart rate, brain wave, amount of perspiration, amount of hormonal secretion, cerebral blood flow, blood pressure, body temperature, electromyogram, respiration, and any other type of the biological signal (including vital information) of the measurement target person 9. The sensor 5 may also be a device configured to analyze blood collected from the measurement target person 9 and outputs a sensor signal S3 indicative of the analysis result. The sensor 5 may also be a device configured to perform body measurement such as jumping for measuring body fatigue or the like.

The input device 6 is an interface for accepting a user input (manual input) of information regarding each measurement target person, and accepts an input of information (e.g., a questionnaire answer) necessary for the measurement of the cognitive function or the estimation of the mental state. Examples of the input device 6 include a touch panel, a button, a keyboard, a mouse, an audio input device, and any other variety of user input interfaces. The input device 6 supplies an input signal "S4" generated based on the input from the user to the information processing device 1.

The information processing device 1A is equipped with the same hardware configuration (see FIG. 1) and functional configuration (see FIG. 3) as the information processing device 1. The cognitive function measurement unit 14 of the information processing device 1A measures the cognitive function of the measurement target person 9 based on the sensor signal S3 or the input signal S4. The mental state estimation unit 15 of the information processing device 1A estimates the mental state of the measurement target person 9 based on the sensor signal S3 or the input signal S4. In this case, examples of the estimation result of the mental state calculated by the mental state estimation unit 15 include the degree of arousal of the measurement target person 9, the degree of stress, the degree of sleepiness, the pulse (heart rate), the degree of concentration, the type of emotion, and the degree of alcohol with respect to the measurement target person 9. It is noted that the degree of stress, the degree of sleepiness, the pulse (heart rate), the degree of concentration, the type of emotion, and the degree of alcohol with respect to the measurement target person 9 are examples of the index of the mental state which affects the cognitive function score like the relation between the degree of arousal and the cognitive function score shown in FIG. 4. In other words, the degree of exertion of the cognitive function of the measurement target person varies depending on the index value (score) of the mental state.

Here, a supplemental description will be given of the measurement of the cognitive function. For example, when the sensor signal S3 is an audio signal, the cognitive function measurement unit 14 measures the cognitive function by analyzing the utterance content of the measurement target person 9 based on the audio signal. It is noted that a technique for measuring a cognitive function by analyzing a free conversation is disclosed in, for example, Patent Literature 2. In another example, when the input signal S4 is information indicating answers to questions used for examining the cognitive function, the cognitive function measurement unit 14 measures the cognitive function based on the information indicating the answers. As an examination of cognitive function based on the subject's answers of questions, for example, Mini Mental State Examination (MMSE) is known.

Then, the cognitive function estimation unit 16 estimates the cognitive function based on the measurement result of the cognitive function outputted by the cognitive function measurement unit 14 and the estimation result of the mental state outputted by the mental state estimation unit 15. Here, as described above, any one of the degree of arousal, the degree of stress, the degree of sleepiness, the pulse (heart rate), the degree of concentration, the type of emotion, and the degree of alcohol with respect to the measurement target person 9 affects the measurement of the cognitive function score. Therefore, the cognitive function estimation unit 16 corrects the cognitive function measurement score Sm calculated by the cognitive function measurement unit 14 by using the estimate value of the mental state estimated by the mental state estimation unit 15. Accordingly, in the same way as in the first example embodiment, the cognitive function estimation unit 16 can suitably calculate the cognitive function estimation score Se independent of the state of the measurement target person 9.

Thus, the information processing device 1A can suitably execute the measurement of the cognitive function of the measurement target person 9 and the estimation of the mental state which affects the measurement, even when the information other than the captured image of the measurement target person 9 is used.

Instead of performing measurement of the cognitive function and estimation of the mental state, the information processing device 1A may acquire the input signal S4 indicating the measurement result of the cognitive function and the estimation result of the mental state which are manually inputted by the user. In this instance, the cognitive function estimation unit 16 of the information processing device 1A calculates the cognitive function estimation score Se based on the cognitive function score and the estimate value of the mental state indicated by the input signal S4. Even according to this mode, the information processing device 1A can suitably estimate the cognitive function independent of the mental state of the measurement target person 9 which changes in the short-term cycles.

Second Modification

The information processing device 1 may function as a server in a client-server model.

Figure 9:
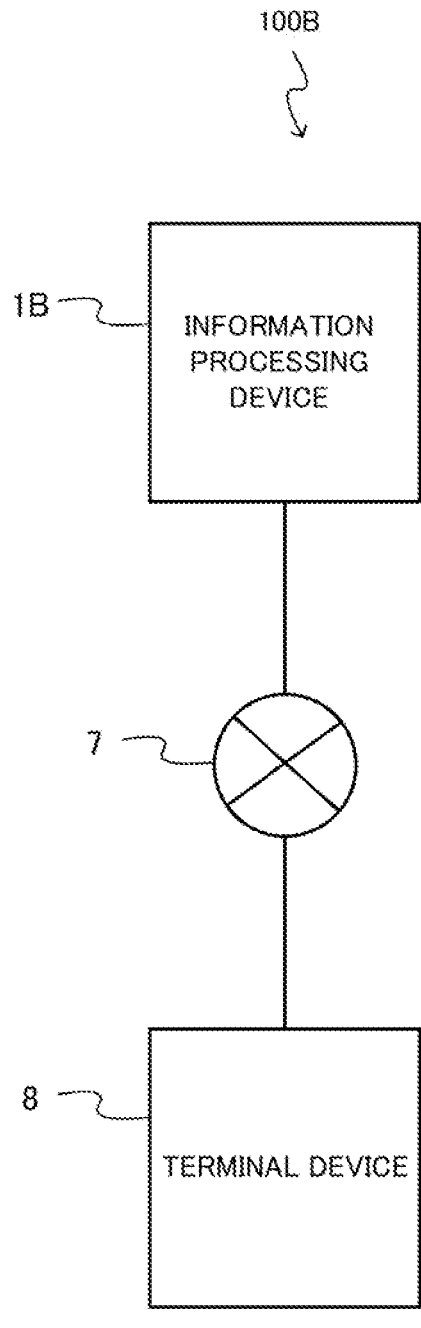
FIG. 9 illustrates a schematic configuration of a cognitive function examination system in a second modification.

FIG. 9 shows a schematic configuration of a cognitive function examination system 100B according to the second modification. The cognitive function examination system 100B mainly includes an information processing device 1B and a terminal device 8 which are configured to perform data communication with each other via the network (communication network) 7. The cognitive function examination system 100B according to the second modification is a system according to a client-server model, wherein the information processing device 1B functions as a server device and the terminal device 8 functions as a client terminal.

The terminal device 8 is a terminal equipped with an input function, a display function, and a communication function, and functions as a display device 3 shown in FIG. 1. Examples of the terminal device 8 include a personal computer, a tablet-type terminal, and a PDA (Personal Digital Assistant). The terminal device 8 supplies the captured image S1 shown in FIG. 1, or, the sensor signal S3 and the input signal S4 shown in FIG. 8 to the information processing device 1B.

The information processing device 1B has the same hardware configuration (see FIG. 1) and functional configuration (see FIG. 3) as the information processing device 1 or the information processing device 1A. Then, based on the information received from the terminal device 8 via the network 7, the information processing device 1B executes each process to be executed by the cognitive function measurement unit 14, the mental state estimation unit 15, the cognitive function estimation unit 16, and the output control unit 17 shown in FIG. 3. Then, the information processing device 1B transmits the display signal S2 indicating the estimation result of the cognitive function or the like to the terminal device 8 via the network 7. Even according to this mode, the information processing device 1B suitably estimates the cognitive function independent of the mental state of the measurement target person 9 that changes in the short-term cycles, and, therefore suitably presents the information on the estimation result to the user of the terminal device 8.

Third Modification

Instead of displaying the examination result screen image on the display device 3, the output control unit 17 may cause an audio output device such as a speaker to output a voice indicative of the estimation result or the like generated by the cognitive function estimation unit 16.

In this instance, the output control unit 17 generates a voice signal for notifying the user of the cognitive function estimation score Se and the like and supplies the voice signal to the audio output device via the interface 13, thereby causing the audio output device to output the voice regarding the cognitive function estimation score Se and the like. Even according to this mode, the output control unit 17 can suitably notify the user of information on the result of the cognitive function examination.

Second Example Embodiment

The cognitive function examination system 100 according to the second example embodiment is different from the cognitive function examination system 100 according to the first example embodiment in that, based on the estimation result of the mental state, it determines the suitability of the examination of the cognitive function and displays information according to the determination result. Hereinafter, the same components as those in the first example embodiment are appropriately denoted by the same reference numerals, and the description thereof will be omitted.

(2-1) Functional Block

Figure 10:
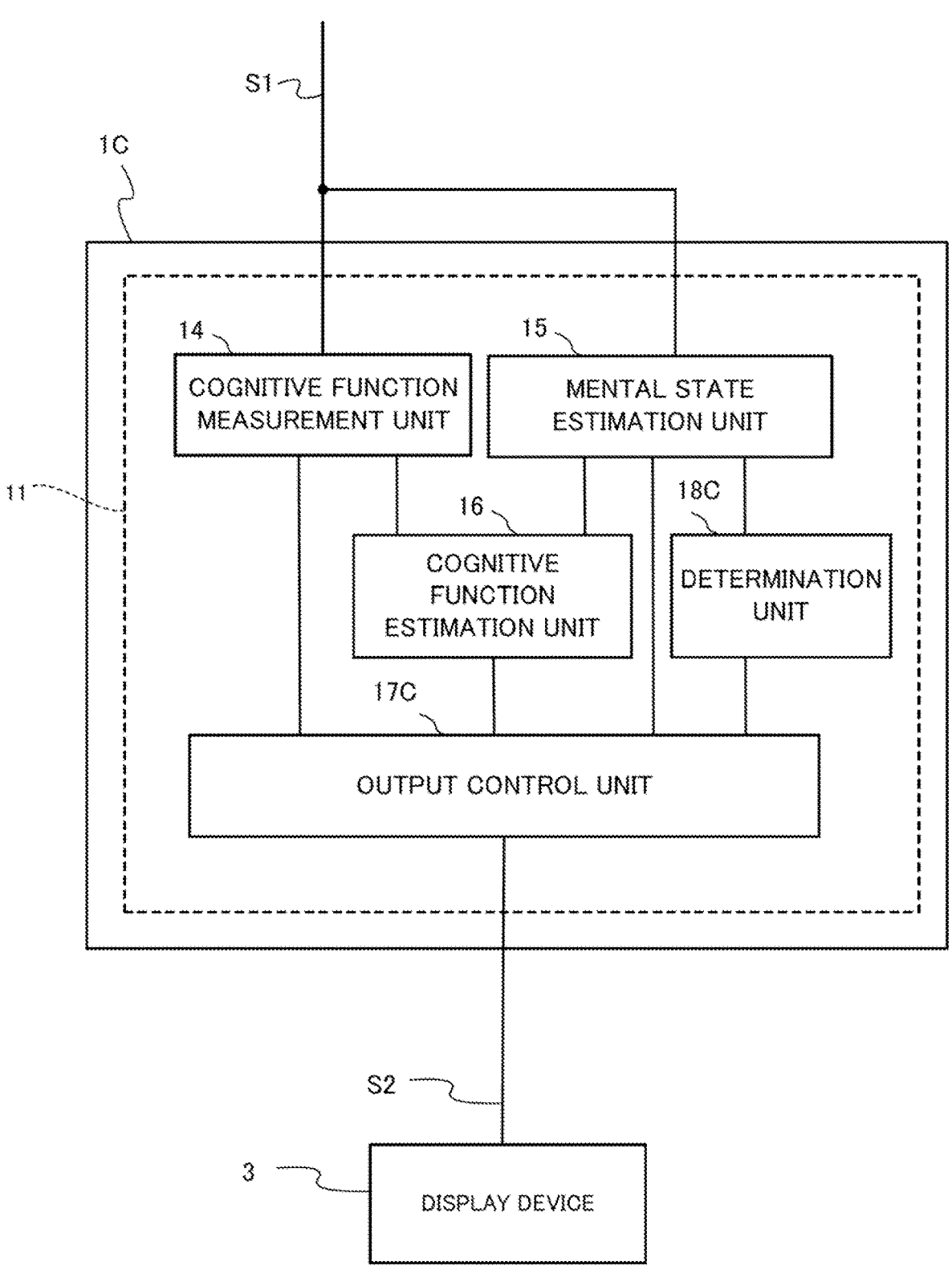
FIG. 10 is a functional block diagram of the information processing device according to a second example embodiment.

FIG. 10 shows a functional block diagram of an information processing device 1C according to the second example embodiment. The information processing device 1C has a hardware configuration shown in FIG. 2, and the processor 11 of the information processing device 1A functionally includes the cognitive function measurement unit 14, the mental state estimation unit 15, the cognitive function estimation unit 16, an output control unit 17C, and a determination unit 18C.

The determination unit 18C determines whether or not the cognitive function examination of the measurement target person 9 is appropriate based on the estimation result of the mental state (hereinafter, the degree of arousal is used as a representative example) of the measurement target person 9 outputted by the mental state estimation unit 15. In other words, the determination unit 18C determines whether or not the measurement target person 9 is in a condition (state)

suitable for taking cognitive function examination (measurement of the cognitive function). In this case, for example, when the degree of arousal estimated by the mental state estimation unit 15 exists within a predetermined value range, the determination unit 18C determines that the measurement target person 9 is in a state in which the measurement of the cognitive function can be appropriately performed. On the other hand, when the degree of arousal estimated by the mental state estimation unit 15 does not exist within the above-described predetermined value range, the determination unit 18C determines that the measurement target person 9 is in a state in which the measurement of the cognitive function cannot be appropriately performed. Here, the "predetermined value range" is the range of the degree of arousal suitable for exertion of the cognitive function by the measurement target person 9, and is previously stored in, for example, the memory 12 or the like. In this case, the "predetermined value range" may be determined based on the difference or ratio between the cognitive function score with the reference arousal degree Dtag and the cognitive function score with the estimated degree of arousal or may be determined to be a range of the degree of arousal such that the estimation error of the cognitive function estimation score Se is within an allowable range. The determination unit 18C supplies the determination result regarding the appropriateness of the cognitive function examination of the measurement target person 9 to the output control unit 17C.

The output control unit 17C generates the display signal S2 on the basis of the measurement result generated by the cognitive function measurement unit 14, the estimation result generated by the mental state estimation unit 15, the estimation result generated by the cognitive function estimation unit 16, and the determination result generated by the determination unit 18C. The output control unit 17C supplies the generated display signal S2 to the display device 3 via the interface 13. Thereby, the output control unit 17C displays the examination result screen image including the content to notify the user of information regarding the appropriateness of the cognitive function examination on the display device 3. Specific examples of the examination result screen image in the second example embodiment will be described later with reference to FIG. 11.

(2-2) Examination Result Screen Image

FIG. 11 illustrates an example of the examination result screen image which the output control unit 17C in the second example embodiment displays on the display device 3. The output control unit 17C causes the display device 3 to display the examination result screen image shown in FIG. 11 by supplying a display signal S2 to the display device 3, wherein the output control unit 17C generates the display signal S2 based on the information supplied from the cognitive function measurement unit 14, the mental state estimation unit 15, the cognitive function estimation unit 16, and the determination unit 18C. The output control unit 17A mainly provides, on the examination result screen image, a notification display field 63 and a score display field 64.

The output control unit 17C displays the content based on the determination result outputted by the determination unit 18C in the notification display field 63. In this example, the output control unit 17C detects the determination that the examination is inappropriate based on the determination result supplied from the determination unit 18C. Then, the output control unit 17C displays, on the notification display field 63, attentions (warnings) indicating that the current state of the measurement target person 9 is unsuitable for the cognitive function examination and that the cognitive function examination should be taken again after a certain period of time.

When the output control unit 17C detects, based on the determination result supplied from the determination unit 18C, that the examination is determined to be appropriate, the output control unit 17C may display in the notification display field 63 a notice indicating, for example, the current state of the measurement target person 9 is suitable for cognitive function examination. In another example, the output control unit 17C may provide the notification display field 63 on the examination result screen image only when the examination is determined by the determination unit 18C to be inappropriate.

Further, in FIG. 11, the output control unit 17C displays the scores relating to the cognitive function and the mental state (degree of arousal in this case) in the score display field 64, respectively. Specifically, the output control unit 17C displays "cognitive function score (measured value)", "degree of arousal", "cognitive function score (estimate value)" and "normal value" which are the same types of scores as the scores displayed in the score display field 60 in FIG. 6. In this case, the cognitive function estimation scoring Se has not been calculated because the examination is determined to be inappropriate. Therefore, the output control unit 17C hides the cognitive function estimation score Se to be displayed in the "cognitive function score (estimate value)".

Thus, according to the display example shown in FIG. 11, when the current state of the measurement target person 9 is not suitable for the cognitive function examination, the output control unit 17C can suitably notify the user of the fact and the necessity of retrying the cognitive function examination.

(2-3) Processing Flow

Figure 12:
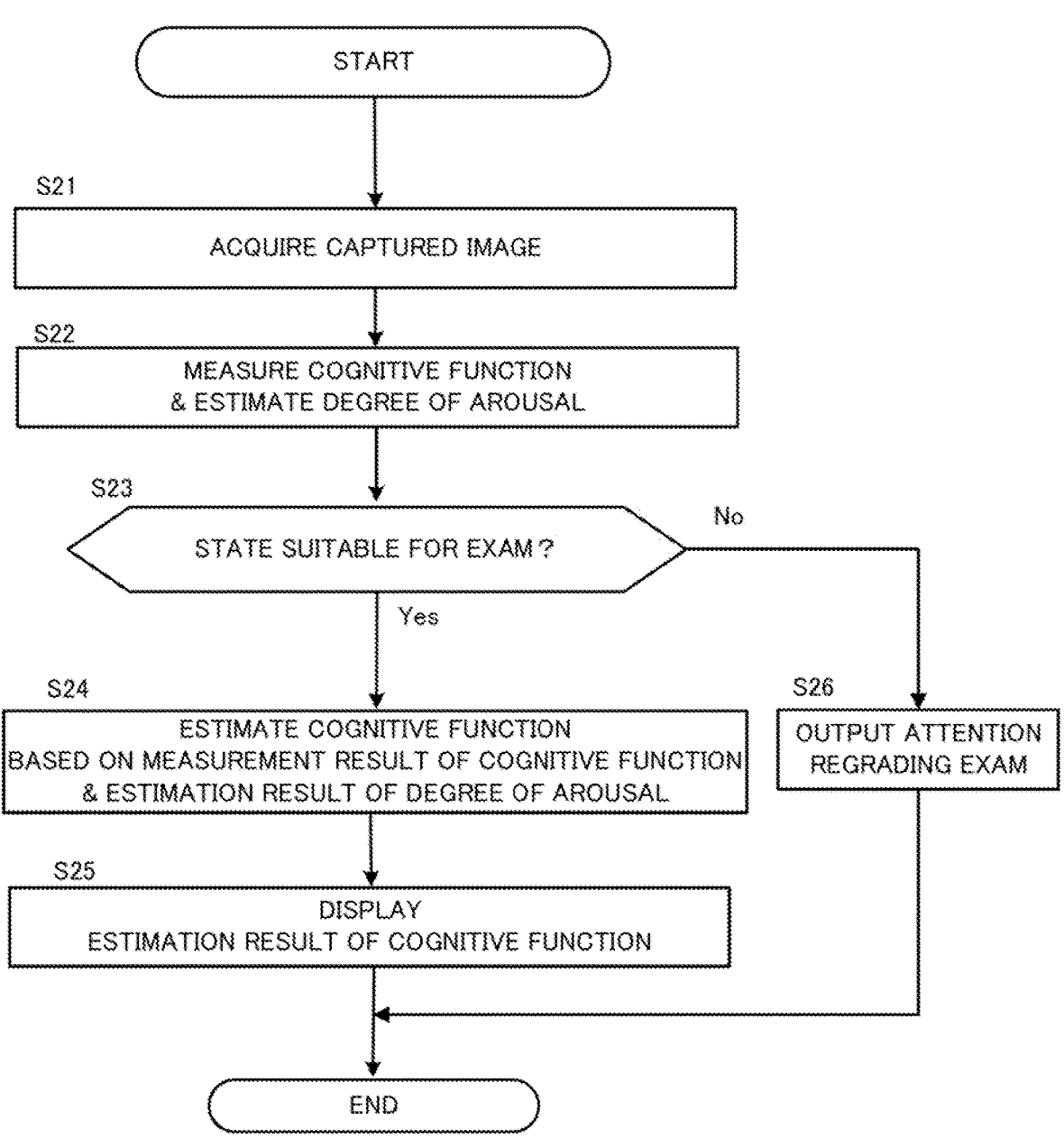
FIG. 12 is an example of a flowchart showing a procedure of the process performed by the information processing device in the second example embodiment.

FIG. 12 illustrates an example of a flowchart indicating a procedure of the process executed by the information processing device 1C in the second example embodiment. The information processing device 1C repeatedly executes the process of the flowchart shown in FIG. 12.

First, the information processing device 1C acquires a captured image S1 generated by the camera 2 (step S21). Then, the cognitive function measurement unit 14 of the information processing device 1 measures the cognitive function based on the captured image S1 acquired at step S21, and the mental state estimation unit 15 of the information processing device 1 estimates the degree of arousal based on the captured image S1 (step S22).

Then, the determination unit 18C determines whether or not the mental state of the measurement target person 9 is a state suitable for the examination based on the degree of arousal estimated at step S22 (step S23). When the determination unit 18C determines that the mental state of the measurement target person 9 is a state suitable for the examination (step S23; Yes), the information processing device 1C performs the same process as the process at step S13 and step S14 in FIG. 7 described in the first example embodiment. Namely, the cognitive function estimation unit 16 estimates the cognitive function based on the measurement result of the cognitive function and the estimation result of the degree of arousal acquired at step S22 (step S24). Then, the output control unit 17C displays the estimated result of the cognitive function on the display device 3 (step S25).

On the other hand, when the determination unit 18C determines that the mental state of the measurement target person 9 is not an mental state suitable for the examination (step S23; No), the output control unit 17C outputs an attention (warning) related to the cognitive function examination (step S26). For example, the output control unit 17C displays, as the above attention, the examination result screen image including the notification display field 63 on the display device 3 as shown in FIG. 11. Thus, when the cognitive function examination is performed in an unsuitable condition, the output control unit 17C can suitably notify the viewer that the appropriate result of the cognitive function examination was not obtained.

The information processing device 1C may estimate the cognitive function at step S24 regardless of the determination result acquired at step S23 and displays the cognitive function estimation score Se at step S26. Even in this case, the information processing device 1C outputs the attention relating to the examination at step S26 thereby to suitably enable the viewer to recognize that the displayed cognitive function estimation score Se is not reliable.

(2-4) Technical Effect

Here, a supplemental description will be given of the technical effects according to the second example embodiment. As described in the first example embodiment with reference to FIGS. 4 and 5, the cognitive function to be measured depends on the mental state such as the degree of arousal of the measurement target person 9 at the time of measurement. Thus, depending on the state of the measurement target person 9 at the time of measurement, such a situation could occur that the measured cognitive function is lower than the original ability. In such a state of the measurement target person 9, the reliability of the cognitive function examination could be low. In view of the above, in the second example embodiment, the information processing device 1C determines whether or not the measurement target person is in a state suitable for the measurement of the intellectual ability based on the degree of arousal, and then outputs a notice related to the reliability of measurement of the cognitive function based on the result of the determination. Accordingly, it is possible to suitably facilitate the measurement target person 9 to receive the cognitive function examination in a suitable condition.

(2-5) Modifications

The following fourth modification and the fifth modification may be applied to the second example embodiment in addition to the first modification to the third modification described in the first example embodiment.

Fourth Modification

The output control unit 17C may output voice or sound, instead of or in addition to displaying the notification display field 63 on the examination result screen image in FIG. 11, which indicates that the measurement target person 9 is not in a state suitable for cognitive function examination and needs a re-examination. In this instance, for example, the output control unit 17C may output the voice equivalent to the text sentence displayed in the notification display field 63 by the audio output device, and/or may output a predetermined warning sound or the like by the audio output device. Even according to this mode, the output control unit 17C may suitably notify the user of the necessity of re-examination and the fact that the measurement target person 9 is not in a condition suitable for the cognitive function examination.

Fifth Modification

In the second example embodiment, the information processing device 1C may not include the cognitive function estimation unit 16.

Generally, when the mental state of the measurement target person 9 is suitable for the examination, it is possible to acquire the cognitive function measurement score Sm in which the inherent cognitive function of the measurement target person 9 is reflected. In consideration of the above, in this modification, when the determination unit 18C determines that the state of the measurement target person 9 is suitable for the examination, the information processing device 1C regards the cognitive function measurement score Sm as the cognitive function estimation score Se and does not calculate the cognitive function estimation score Se by the cognitive function estimation unit 16. Even in this instance, the information processing device 1C can suitably present the user with the cognitive function score that is not substantially affected by the change in the mental state of the measurement target person 9 in the short-term cycles.

Third Example Embodiment

Figure 13:
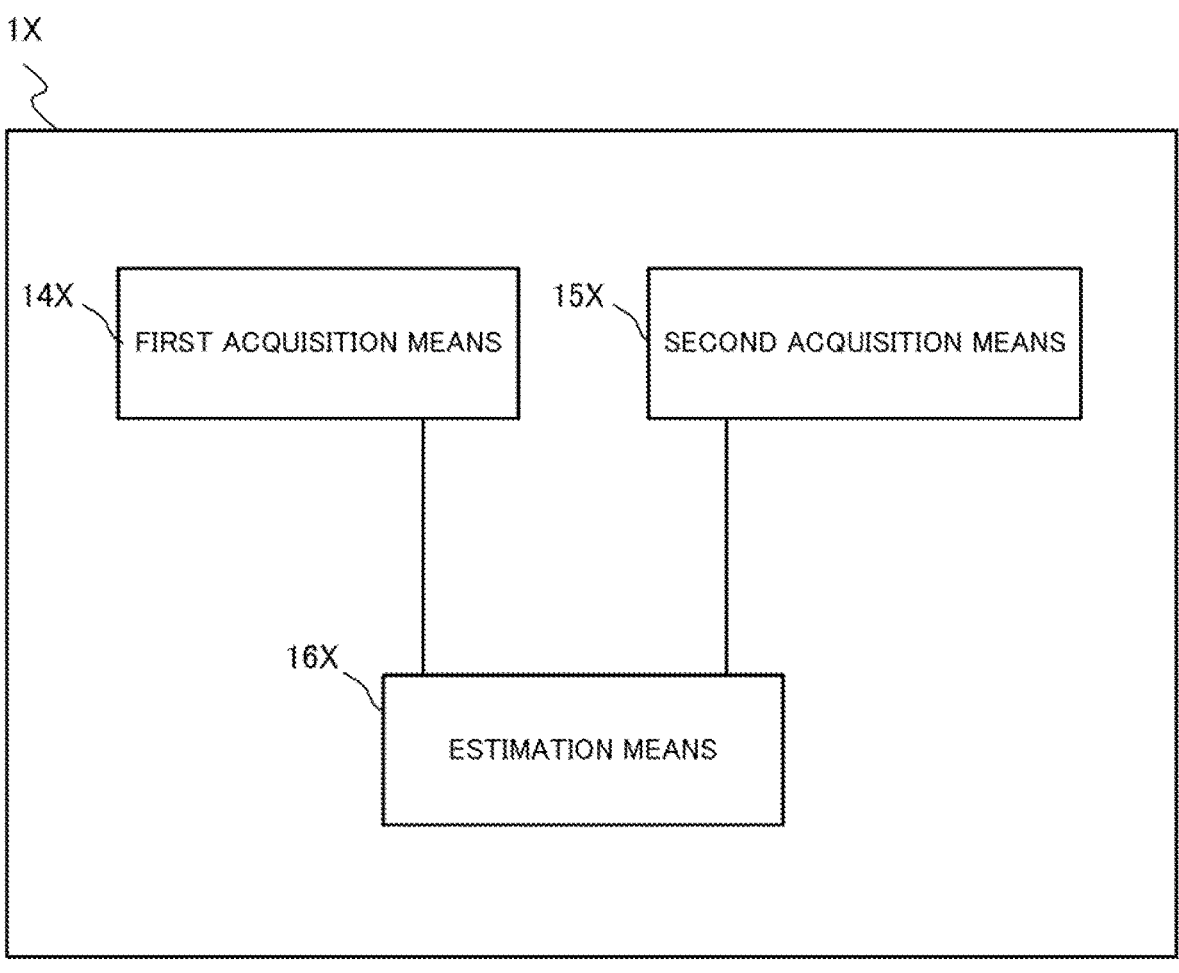
FIG. 13 is a schematic configuration diagram of the information processing device according to a third example embodiment.

FIG. 13 is a schematic configuration diagram of an information processing device 1X according to the third example embodiment. The information processing device 1X mainly includes a first acquisition means 14X, a second acquisition means 15X, and an estimation means 16X. The information processing device 1X may be configured by a plurality of devices.

The first acquisition means 14X is configured to acquire a measurement result of an intellectual ability of a measurement target person. Here, the term "measurement result of an intellectual ability" includes not only a measurement result of an ability measured in an examination of cognitive impairment or major neurocognitive disorder, but also a measurement result of an intellectual ability measured in an aptitude test carried out as a part of an entry test of a company, and a result of an intellectual skill measured in an English skill test and the like. For example, the first acquisition means 14X may be the cognitive function measurement unit 14 in the first example embodiment (including the case where any of the modifications is applied, the same shall apply hereinafter) or the second example embodiment (including the case where any of the modifications is applied, the same shall apply hereinafter). The first acquisition means 14X may also acquire the measurement result of the intellectual ability of the measurement target person by receiving the measurement result of the intellectual ability of the measurement target person from another device.

The second acquisition means 15X is configured to acquire an estimation result of a mental state of the measurement target person, the mental state affecting the measurement of the intellectual ability. The term "mental state affecting the measurement of intellectual ability" indicates one aspect of the mental state of the measurement target person, and corresponds to what fluctuates depending on the time such as the degree of arousal, the degree of stress, the degree of concentration, the type of emotion and the degree of sleepiness. For example, the second acquisition means 15X may be the mental state estimation unit 15 in the first example embodiment or the second example embodiment. The second acquisition means 15X may acquire the estimation result by receiving the estimation result of the mental state of the measurement target person affecting the measurement of the intellectual ability from another device.

The estimation means 16X is configured to estimate the intellectual ability based on the measured result of intellectual ability and the estimation result of the mental state. For example, the estimation unit 16X may be the cognitive function estimation unit 16 according to the first example embodiment or the second example embodiment.

Figure 14:
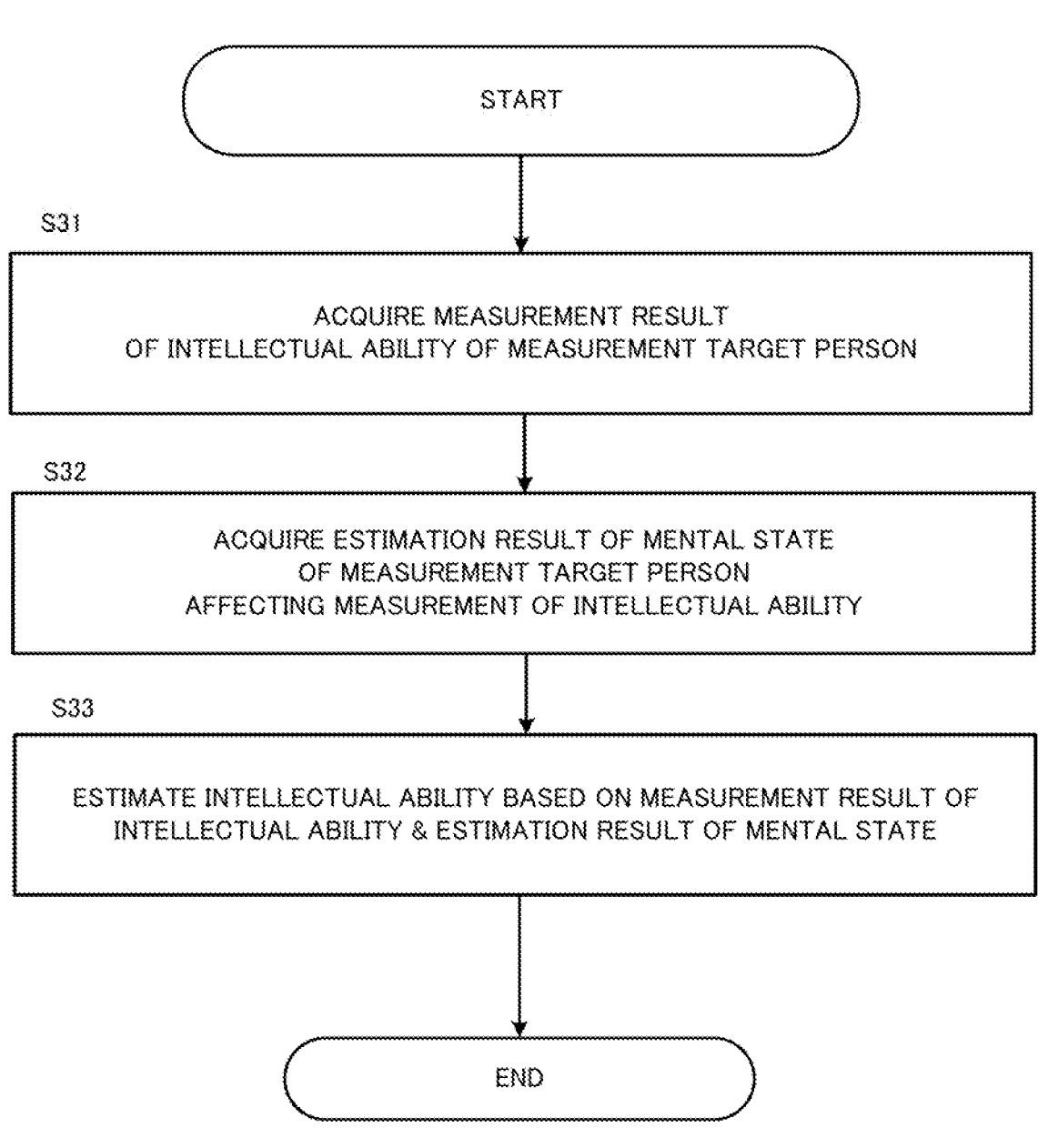
FIG. 14 illustrates an example of a flowchart showing a procedure of the process performed by the information processing device in the third example embodiment.

FIG. 14 is an exemplary flowchart that is executed by the information processing device 1X in the third example embodiment. The first acquisition means 14X acquires a measurement result of an intellectual ability of a measurement target person (step S31). Next, the second acquisition means 15X acquires an estimation result of a mental state of the measurement target person, the mental state affecting the measurement of the intellectual ability (step S32). The estimation means 16X estimates the intellectual ability based on the measured result of intellectual ability and the estimation result of the mental state (step S33).

According to the third example embodiment, the information processing device 1X can suitably perform the estimation of the intellectual ability independent of the state (condition) of the measurement target person.

Fourth Example Embodiment

Figure 15:
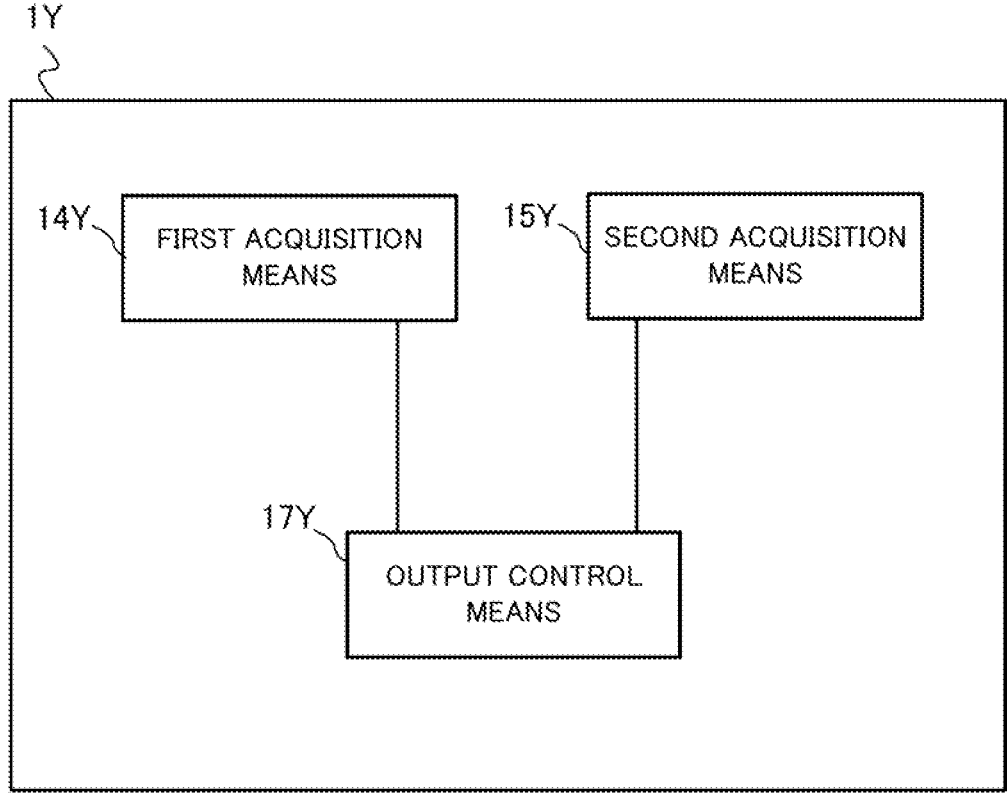
FIG. 15 is a schematic configuration diagram of the information processing device according to a fourth example embodiment.

FIG. 15 shows a schematic configuration diagram of an information processing device 1Y according to the fourth example embodiment. The information processing device 1Y mainly includes a first acquisition means 14Y, a second acquisition means 15Y, and an output control means 17Y. The information processing device 1Y may be configured by a plurality of devices.

The first acquisition means 14Y is configured to acquire a measurement result of an intellectual ability of a measurement target person. For example, the first acquisition means 14Y may be the cognitive function measurement unit 14 in the first example embodiment (including the case where any of the modifications is applied, the same shall apply hereinafter) or the second example embodiment (including the case where any of the modifications is applied, the same shall apply hereinafter). The first acquisition means 14Y may also acquire the measurement result of the intellectual ability of the measurement target person by receiving the measurement result of the intellectual ability of the measurement target person from another device.

The second acquisition means 15Y is configured to acquire an estimation result of a mental state of the measurement target person, the mental state affecting the measurement of the intellectual ability. For example, the second acquisition means 15Y may be the mental state estimation unit 15 in the first example embodiment or the second example embodiment. The second acquisition means 15Y may acquire the estimation result by receiving the estimation result of the mental state of the measurement target person affecting the measurement of the intellectual ability from another device.

The output control means 17Y is configured to display or output, by audio, information on the measurement result of the intellectual ability based on the estimation result of the mental state. The term "information on the measurement result of the intellectual ability" may be the cognitive function measurement score Sm, the cognitive function estimation score Se or both in the second example embodiment, or may be the notice displayed in the notification display field 63 in FIG. 11. The mode to "display or output by audio" is not limited to a mode in which the output control means 17Y outputs a display or an audio by itself, but includes a mode in which the output control means 17Y transmits a control signal to any other processing unit in the information processing device or to an external device other than the information processing device to thereby cause it to perform a display or an audio output. The output control means 17Y may be the output control unit 17C in the second example embodiment.

Figure 16:
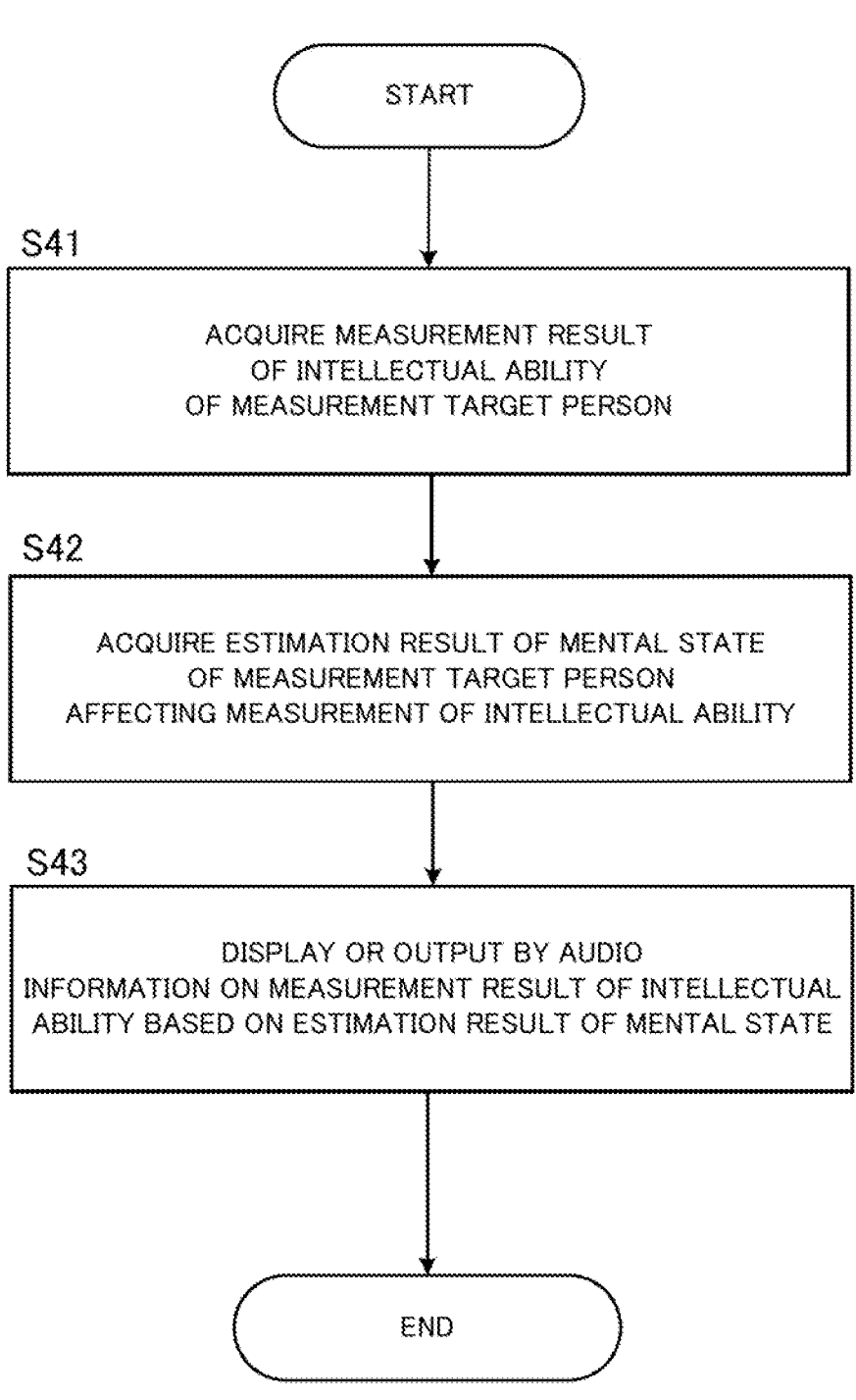
FIG. 16 illustrates an example of a flowchart showing a procedure of the process performed by the information processing device in the fourth example embodiment.

FIG. 16 is an exemplary flowchart that is executed by the information processing device 1Y in the fourth example embodiment. The first acquisition means 14Y of the information processing device 1Y acquires a measurement result of an intellectual ability of a measurement target person (step S41). Next, the second acquisition means 15Y acquires an estimation result of a mental state of the measurement target person, the mental state affecting the measurement of the intellectual ability (step S42). The output control means 17Y displays or outputs, by audio, information on the measurement result of the intellectual ability based on the estimation result of the mental state (step S43).

According to the fourth example embodiment, the information processing device 1Y can suitably present the information on the measurement result of the intellectual ability of the measurement target person to the user based on the estimation result of the mental state of the measurement target person that affects the measurement of the intellectual ability.

In the example embodiments described above, the program is stored by any type of a non-transitory computer-readable medium (non-transitory computer readable medium) and can be supplied to a control unit or the like that is a computer. The non-transitory computer-readable medium include any type of a tangible storage medium. Examples of the non-transitory computer readable medium include a magnetic storage medium (e.g., a flexible disk, a magnetic tape, a hard disk drive), a magnetic-optical storage medium (e.g., a magnetic optical disk), CD-ROM (Read Only Memory), CD-R, CD-R/W, a solid-state memory (e.g., a mask ROM, a PROM (Programmable ROM), an EPROM (Erasable PROM), a flash ROM, a RAM (Random Access Memory)). The program may also be provided to the computer by any type of a transitory computer readable medium. Examples of the transitory computer readable medium include an electrical signal, an optical signal, and an electromagnetic wave. The transitory computer readable medium can provide the program to the computer through a wired channel such as wires and optical fibers or a wireless channel.

The whole or a part of the example embodiments (including modifications, the same shall apply hereinafter) described above can be described as, but not limited to, the following Supplementary Notes.

Supplementary Note 1

An information processing device comprising:
a first acquisition means configured to acquire a measurement result of an intellectual ability of a measurement target person;
a second acquisition means configured to acquire an estimation result of a mental state of the measurement target person, the mental state affecting the measurement of the intellectual ability; and an estimation means configured to estimate the intellectual ability based on the measured result of intellectual ability and the estimation result of the mental state.

Supplementary Note 2

The information processing device according to Supplementary Note 1,
wherein the second acquisition means is configured to acquire the estimation result of the mental state which indicates at least one of a degree of arousal, a pulse, a degree of sleepiness, a type of emotion, or a degree of alcohol during the measurement of the intellectual ability of the measurement target person.

Supplementary Note 3

The information processing device according to Supplementary Note 1 or 2,
wherein the measurement result of the intellectual ability indicates a score representing the intellectual ability, and
wherein the estimation means is configured to calculate the estimation result of the intellectual ability that indicates a corrected score obtained by correcting the score representing the intellectual ability based on the estimation result of the mental state.

Supplementary Note 4

The information processing device according to any one of Supplementary Notes 1 to 3,
wherein the estimation means is configured to estimate the intellectual ability based on a degree of exertion of the intellectual ability, the degree of exertion being estimated based on the estimation result of the mental state.

Supplementary Note 5

The information processing device according to any one of Supplementary Notes 1 to 4,
wherein the first acquisition means is configured to generate the measurement result of the intellectual ability that is a measurement result of a cognitive function of the measurement target person based on an image generated by an imaging means configured to image the measurement target person, and
wherein the second acquisition means is configured to generate the estimation result of the mental state based on the image.

Supplementary Note 6

The information processing device according to any one of Supplementary Notes 1 to 5, further comprising
an output control means configured to display or output by audio the estimation result of the intellectual ability generated by the estimation means.

Supplementary Note 7

The information processing device according to Supplementary Note 6,
wherein the output control means is configured to display or output by audio at least one of the measurement result of the intellectual ability or the information representing a normal value of the intellectual ability and
the estimation result of the intellectual ability.

Supplementary Note 8

The information processing device according to Supplementary Note 6 or 7, further comprising
a determination means configured to make a determination, based on the estimation result of the mental state, on whether or not the measurement target person is in a state suitable for the measurement of the intellectual ability,
wherein the output control means is configured to give a notice regarding the measurement of the intellectual ability based on a result of the determination.

Supplementary Note 9

The information processing device according to any one of Supplementary Notes 6 to 8,
wherein the estimation means is configured to estimate the cognitive function of the measurement target person, and
wherein the output control means is configured to display or output by audio information on the possibility of cognitive impairment of the measurement target person based on an estimation result of the cognitive function and a criterion regarding the cognitive impairment.

Supplementary Note 10

The information processing device according to any one of Supplementary Notes 1 to 9, further comprising
a third acquisition means configured to acquire information on an age of the measurement target person,
wherein the estimation means is configured to estimate the intellectual ability based on
the measurement result of the intellectual ability,
the estimation result of the mental state, and
the information on the age.

Supplementary Note 11

An information processing device comprising:
a first acquisition means configured to acquire a measurement result of an intellectual ability of a measurement target person;
a second acquisition means configured to acquire an estimation result of a mental state of the measurement target person, the mental state affecting the measurement of the intellectual ability; and
an output control means configured to display or output, by audio, information on the measurement result of the intellectual ability based on the estimation result of the mental state.

Supplementary Note 12

The information processing device according to Supplementary Note 11, further comprising
a determination means configured to make a determination, based on the estimation result of the mental state, on whether or not the measurement target person is in a state suitable for the measurement of the intellectual ability, wherein, when it is determined that the measurement target person is not in the state suitable for the measurement of the intellectual ability, the output control means is configured to display or output by audio, as the information on the measurement result of the intellectual ability, an attention relating to the measurement of the intellectual ability.

Supplementary Note 13

The information processing device according to Supplementary Note 11 or 12, further comprising
a determination means configured to make a determination, based on the estimation result of the mental state, on whether or not the measurement target person is in a state suitable for the measurement of the intellectual ability,
wherein, when it is determined that the measurement target person is in the state suitable for the measurement of the intellectual ability, the output control means is configured to display, as the information on the measurement result of the intellectual ability, at least one of
the measurement result of the intellectual ability, or
an estimation result of the intellectual ability generated based on the measurement result of the intellectual ability and the estimation result of the mental state.

Supplementary Note 14

A control method executed by an information processing device, the control method comprising:
acquiring a measurement result of an intellectual ability of a measurement target person;
acquiring an estimation result of a mental state of the measurement target person, the mental state affecting the measurement of the intellectual ability; and
estimating the intellectual ability based on the measured result of intellectual ability and the estimation result of the mental state.

Supplementary Note 15

A storage medium storing a program executed by a computer, the program causing the computer to
acquire a measurement result of an intellectual ability of a measurement target person;
acquire an estimation result of a mental state of the measurement target person, the mental state affecting the measurement of the intellectual ability; and
estimate the intellectual ability based on the measured result of intellectual ability and the estimation result of the mental state.

Supplementary Note 16

A control method executed by an information processing device, the control method comprising:
acquiring a measurement result of an intellectual ability of a measurement target person;
acquiring an estimation result of a mental state of the measurement target person, the mental state affecting the measurement of the intellectual ability; and
displaying or outputting, by audio, information on the measurement result of the intellectual ability based on the estimation result of the mental state.

Supplementary Note 17

A storage medium storing a program executed by a computer, the program causing the computer to acquire a measurement result of an intellectual ability of a measurement target person;

acquire an estimation result of a mental state of the measurement target person, the mental state affecting the measurement of the intellectual ability; and display or output, by audio, information on the measurement result of the intellectual ability based on the estimation result of the mental state.

While the invention has been particularly shown and described with reference to example embodiments thereof, the invention is not limited to these example embodiments. It will be understood by those of ordinary skilled in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. All Patent and Non-Patent Literatures mentioned in this specification are incorporated by reference in its entirety.

DESCRIPTION OF REFERENCE NUMERALS 1, 1A, 1B, 1X, 1Y Information processing device
2 Camera (imaging means)
3 Display device
5 Sensor
6 Input device
7 Network
8 Terminal device
100, 100A, 100B Cognitive function examination system

What is claimed is:

1. An information processing device comprising:
at least one memory configured to store instructions; and
at least one processor configured to execute the instructions to:

acquire a captured image of an eyeball of a measurement target person under measurement while the measurement target person is viewing a test screen;

calculate, based on the acquired captured image, a cognitive function measurement score of the measurement target person by performing image analysis of a movement of the eyeball of the measurement target person in the acquired captured image;

estimate, based on the acquired captured image, an arousal level of the measurement target person at a time of cognitive function measurement by analyzing, using a deep learning model, a facial expression or a movement of an eyelid of the measurement target person in the acquired captured image, the deep learning model trained based on facial image data of measurement target persons under measurement and arousal levels of the measurement target persons under measurement at timing in which the facial image data was captured;

and correct the calculated cognitive function measurement score by applying, based on the estimated arousal level, a correction derived from a stored statistical model, thereby:

generating a cognitive function estimation score; and compensating for a temporary decrease in cognitive function of the measurement target person caused by a non-optimal arousal level.

2. The information processing device according to claim 1, wherein the at least one processor is configured to execute the instructions to acquire a pulse, a degree of sleepiness, a type of emotion, or a degree of alcohol of the measurement target person.

3. The information processing device according to claim 1, wherein the at least one processor is configured to execute the instructions to generate the cognitive function estimation score based on a degree of exertion of the cognitive function, the degree of exertion being estimated based on the estimated arousal level.

4. The information processing device according to claim 1, wherein the at least one processor is configured to further execute the instructions to display or output by audio the cognitive function estimation score.

5. The information processing device according to claim 4, wherein the at least one processor is configured to execute the instructions to display or output by audio;

at least one of the calculated cognitive function measurement score or information representing a normal value of the cognitive function; and the cognitive function estimation score.

6. The information processing device according to claim 4, wherein the at least one processor is configured to further execute the instructions to make a determination, based on the cognitive function estimation score, on whether or not the measurement target person is in a state suitable for the cognitive function measurement, wherein the at least one processor is configured to execute the instructions to give a notice regarding the measurement based on a result of the determination.

7. The information processing device according to claim 4, wherein the at least one processor is configured to execute the instructions to estimate the cognitive function of the measurement target person, and wherein the at least one processor is configured to execute the instructions to display or output by audio information on the possibility of cognitive impairment of the measurement target person based on the cognitive function estimation score and a criterion regarding the cognitive impairment.

8. The information processing device according to claim 1, wherein the at least one processor is configured to further execute the instructions to acquire information on an age of the measurement target person, and wherein the at least one processor is configured to execute the instructions to generate the cognitive function estimation score based on:

the cognitive function measurement score, the estimated arousal level, and the information on the age.

9. An information processing device comprising:
at least one memory configured to store instructions; and
at least one processor configured to execute the instructions to:

acquire a captured image of an eyeball of a measurement target person under measurement while the measurement target person is viewing a test screen;

calculate, based on the acquired captured image, a cognitive function measurement score of the measurement target person by performing image analysis of a movement of the eyeball of the measurement target person in the acquired captured image;

estimate, based on the acquired captured image, an arousal level of the measurement target person at a time of cognitive function measurement by analyzing, using a deep learning model, a facial expression or a movement of an eyelid of the measurement target person in the acquired captured image, the deep learning model trained based on facial image data of measurement target persons under measurement and arousal levels of the measurement target persons under measurement at timing in which the facial image data was captured;

determine, based on the estimated arousal level, whether or not the measurement target person is in a state suitable for the cognitive function measurement, upon determining that the measurement target person is in the state suitable for the cognitive function measurement, display or output by audio information on the cognitive function measurement score; and upon determining that the measurement target person is not in the state suitable for the cognitive function measurement, display or output by audio a warning relating to the cognitive function measurement.

10. The information processing device according to claim 9, wherein, upon determining that the measurement target person is in the state suitable for the cognitive function measurement, the at least one processor is configured to execute the instructions to display at least one of:

the calculated cognitive function measurement score, or a corrected cognitive function measurement score based on the estimated arousal level.

11. A control method executed by an information processing device, the control method comprising:

acquiring a captured image of an eyeball of a measurement target person under measurement while the measurement target person is viewing a test screen;

calculating, based on the acquired captured image, a cognitive function measurement score of the measurement target person by performing image analysis of a movement of the eyeball of the measurement target person in the acquired captured image, based on the acquired captured image;

estimating, based on the acquired captured image, an arousal level of the measurement target person at a time of cognitive function measurement by analyzing, using a deep learning model, a facial expression or a movement of an eyelid of the measurement target person in the acquired captured image, the deep learning model trained based on facial image data of measurement target persons and arousal levels of the measurement target persons under measurement at timing in which the facial image data was captured;

correcting the calculated cognitive function measurement score by applying, based on the estimated arousal level, a correction derived from a stored statistical model, thereby:

generating a cognitive function estimation score; and compensating for a temporary decrease in cognitive function of the measurement target person caused by a non-optimal arousal level.

* * * * *